(12) United States Patent
Frantzen et al.

(10) Patent No.: US 6,776,783 B1
(45) Date of Patent: Aug. 17, 2004

(54) SURGICAL CLIPS AND APPARATUS AND METHOD FOR CLIP PLACEMENT

(75) Inventors: John J. Frantzen, Laguna Niguel, CA (US); Charles S. Taylor, San Francisco, CA (US); Michael V. Morejohn, San Jose, CA (US); Dwight P. Morejohn, Davis, CA (US); Ronald Devore, Los Gatos, CA (US)

(73) Assignee: CardioThoracic Systems, Inc., Santa Clara, CA (US)

( * ) Notice: Subject to any disclaimer, the term of this patent is extended or adjusted under 35 U.S.C. 154(b) by 0 days.

(21) Appl. No.: 09/747,636

(22) Filed: Dec. 21, 2000

Related U.S. Application Data

(63) Continuation of application No. 09/226,662, filed on Jan. 8, 1999, now Pat. No. 6,193,732.

(51) Int. Cl.[7] .............................................. A61B 17/08
(52) U.S. Cl. ........................ 606/151; 606/142; 606/157; 606/158
(58) Field of Search ................................ 606/151, 157, 606/158, 142, 139; 24/545–547, 563, 572, 573, 536

(56) References Cited

U.S. PATENT DOCUMENTS

| | | | |
|---|---|---|---|
| 3,006,344 A | 10/1961 | Vogelfanger | 128/318 |
| 3,175,556 A | 3/1965 | Wood et al. | 128/305 |
| 3,545,444 A | 12/1970 | Green | 128/305 |
| 3,584,628 A | 6/1971 | Green | 128/305 |
| 3,608,544 A | 9/1971 | Schnepper | 128/2 R |
| 3,665,924 A | 5/1972 | Noiles et al. | 128/305 |
| 3,675,688 A | 7/1972 | Bryan et al. | 140/93 D |
| 4,086,926 A | 5/1978 | Green et al. | 128/334 |
| 4,274,415 A | 6/1981 | Kanamoto et al. | 128/321 |
| 4,416,266 A * | 11/1983 | Baucom | 606/158 |
| 4,444,187 A | 4/1984 | Perlin | 128/346 |
| 4,556,058 A | 12/1985 | Green | 128/30 |
| 4,557,263 A | 12/1985 | Green | 128/325 |
| 4,569,346 A | 2/1986 | Poirier | 128/305 |
| 4,579,118 A | 4/1986 | Failla | 128/325 |
| 4,620,541 A | 11/1986 | Gertzman et al. | 128/326 |
| 4,777,949 A | 10/1988 | Perlin | 128/325 |
| 4,777,950 A | 10/1988 | Kees, Jr. | 128/325 |
| 4,791,707 A | 12/1988 | Tucker | 227/19 |
| 4,796,627 A | 1/1989 | Tucker | 128/337 |
| 4,799,481 A | 1/1989 | Transue et al. | 128/325 |
| 4,834,096 A | 5/1989 | Oh et al. | 128/325 |
| 4,957,500 A | 9/1990 | Liang et al. | 606/157 |
| 4,961,743 A | 10/1990 | Kees, Jr. et al. | 606/158 |
| 4,966,603 A | 10/1990 | Focelle et al. | 606/158 |
| 5,053,045 A | 10/1991 | Schmidt et al. | 606/157 |
| 5,062,848 A | 11/1991 | Frazee et al. | 606/213 |
| 5,160,339 A | 11/1992 | Chen et al. | 606/158 |
| 5,192,288 A | 3/1993 | Thompson et al. | 606/143 |
| 5,197,970 A | 3/1993 | Green et al. | 606/158 |
| 5,201,746 A | 4/1993 | Shichman | 606/151 |
| 5,207,691 A | 5/1993 | Nardella | 606/142 |
| 5,234,449 A | 8/1993 | Bruker et al. | 606/158 |
| 5,242,456 A * | 9/1993 | Nash et al. | 606/151 |
| 5,282,811 A | 2/1994 | Booker et al. | 606/157 |
| 5,282,812 A | 2/1994 | Suarez, Jr. | 606/158 |
| 5,304,183 A | 4/1994 | Gourlay et al. | 606/142 |

(List continued on next page.)

*Primary Examiner*—Julian W. Woo
(74) *Attorney, Agent, or Firm*—Fenwick & West LLP

(57) ABSTRACT

An improved surgical clip and clip applicator for placing a surgical clip over a target structure. The surgical clip generally has a pair of opposing clamp arms, each having an associated clamping surface, and a connecting portion joining the clamp arms and biasing them to a normally closed position. The surgical clip may be opened and locked into the open position prior to being loaded into a clip applicator or the surgical clip may be opened by a clip applicator itself. The surgical clip and clip applicators require reduced actuation forces and simplified applicator mechanisms.

6 Claims, 12 Drawing Sheets

U.S. PATENT DOCUMENTS

| | | | |
|---|---|---|---|
| 5,306,280 A | 4/1994 | Bregen et al. | 606/143 |
| 5,312,426 A | 5/1994 | Segawa et al. | 606/158 |
| 5,330,442 A | 7/1994 | Green et al. | 606/232 |
| 5,342,373 A | 8/1994 | Stefanchik et al. | 606/142 |
| 5,366,458 A | 11/1994 | Korthoff et al. | 606/151 |
| 5,368,600 A | 11/1994 | Failla et al. | 606/139 |
| 5,571,121 A | 11/1996 | Heifetz | 606/158 |
| 5,593,414 A | 1/1997 | Shipp et al. | 606/142 |
| 5,601,574 A | 2/1997 | Stefanchik et al. | 606/143 |
| 5,607,436 A | 3/1997 | Pratt et al. | 606/143 |
| 5,634,932 A | 6/1997 | Schmidt | 606/157 |
| 5,683,405 A | 11/1997 | Yacoubian et al. | 606/158 |
| 5,695,505 A | 12/1997 | Yoon | 606/157 |
| 5,755,726 A | 5/1998 | Pratt et al. | 606/143 |
| 5,758,420 A | 6/1998 | Schmidt et al. | 29/896.9 |
| 5,792,149 A | 8/1998 | Sherts et al. | 606/142 |
| 5,827,306 A | 10/1998 | Yoon | 606/159 |
| 5,843,101 A | 12/1998 | Fry | 606/157 |
| 5,858,018 A | 1/1999 | Shipp et al. | 606/142 |

* cited by examiner

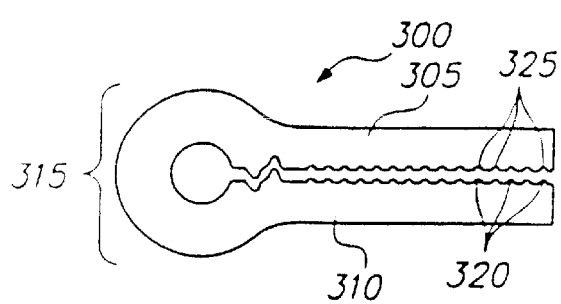
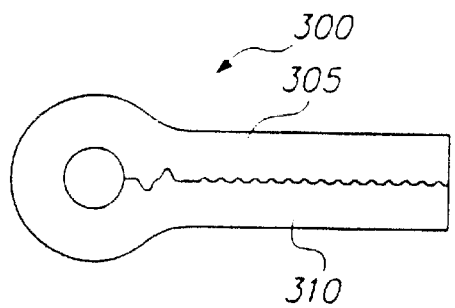
*FIG. 6A*  *FIG. 6B*
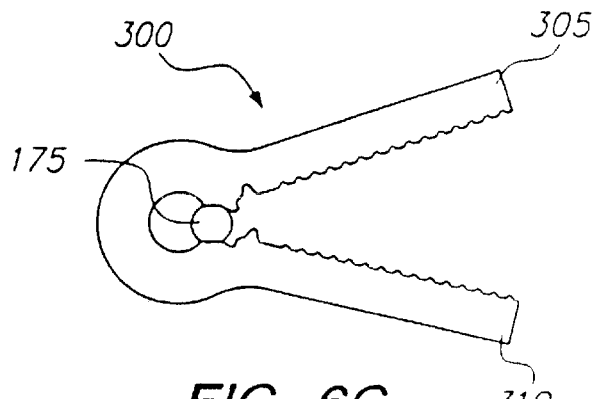
*FIG. 6C*
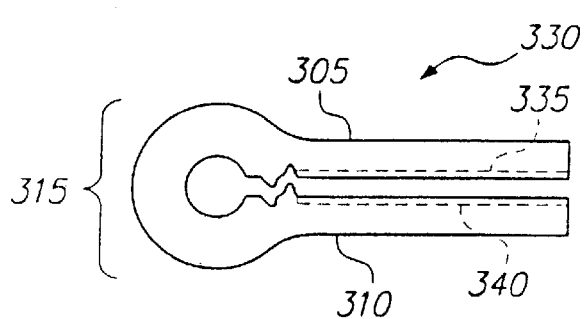
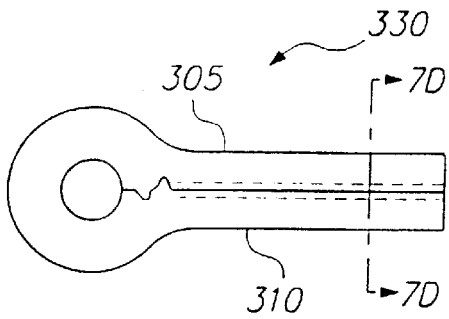
*FIG. 7A*  *FIG. 7B*
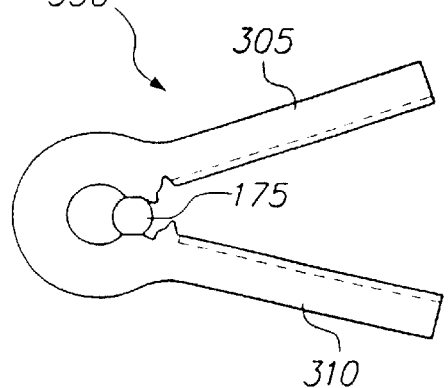
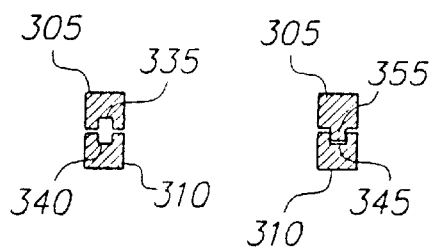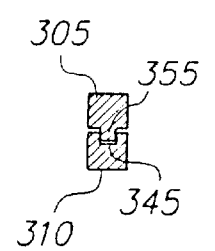
*FIG. 7C*  *FIG. 7D*  *FIG. 7E*

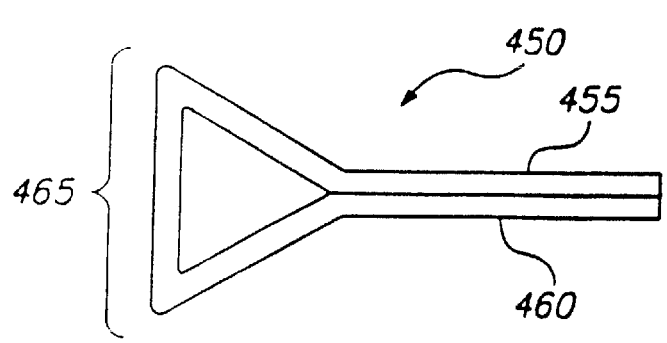 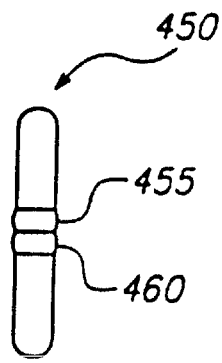
FIG. 11A  FIG. 11B
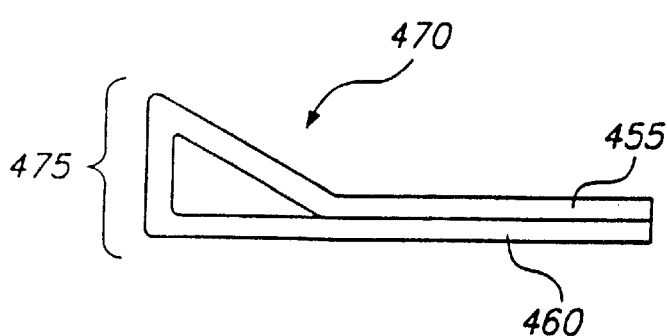 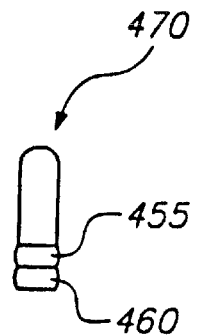
FIG. 12A  FIG. 12B
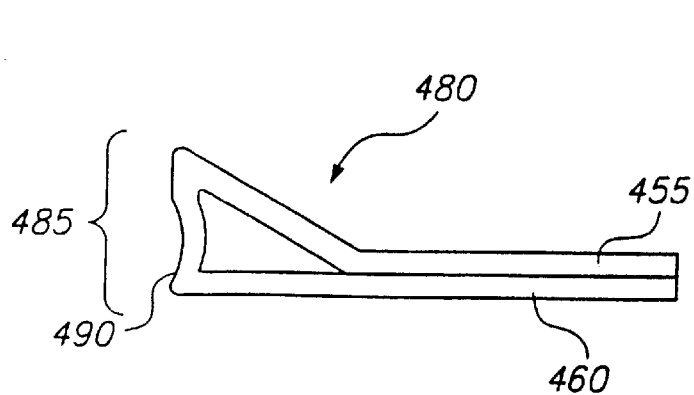 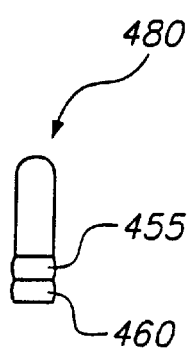
FIG. 13A  FIG. 13B

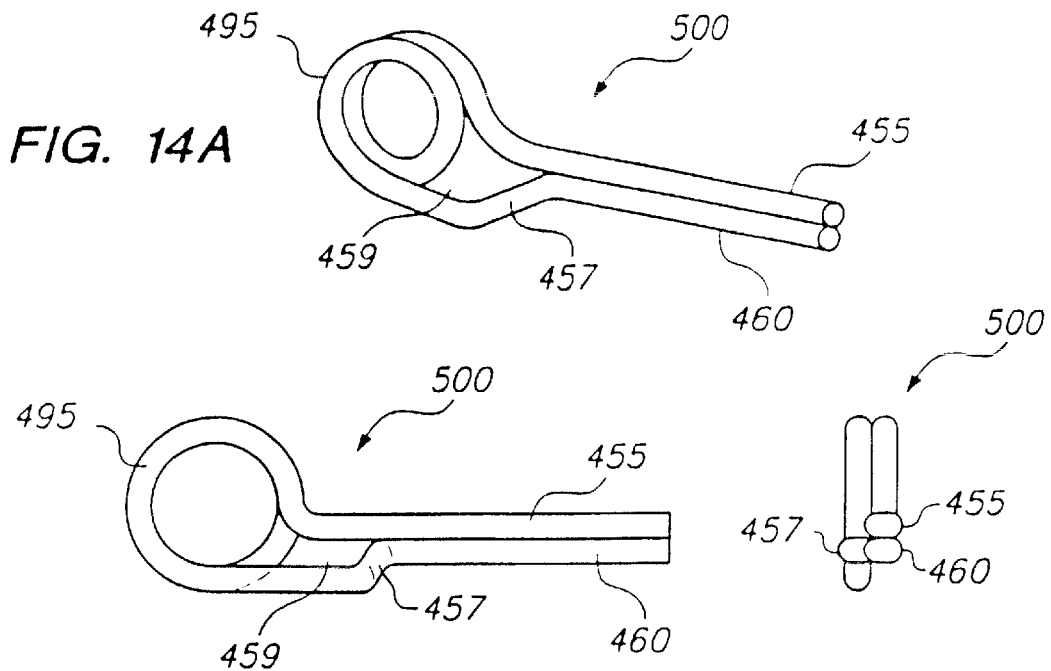
FIG. 14A
FIG. 14B
FIG. 14C
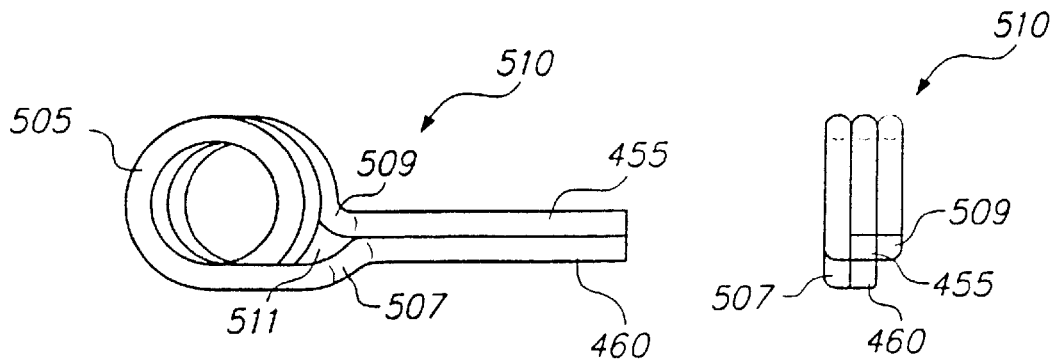
FIG. 15A
FIG. 15B
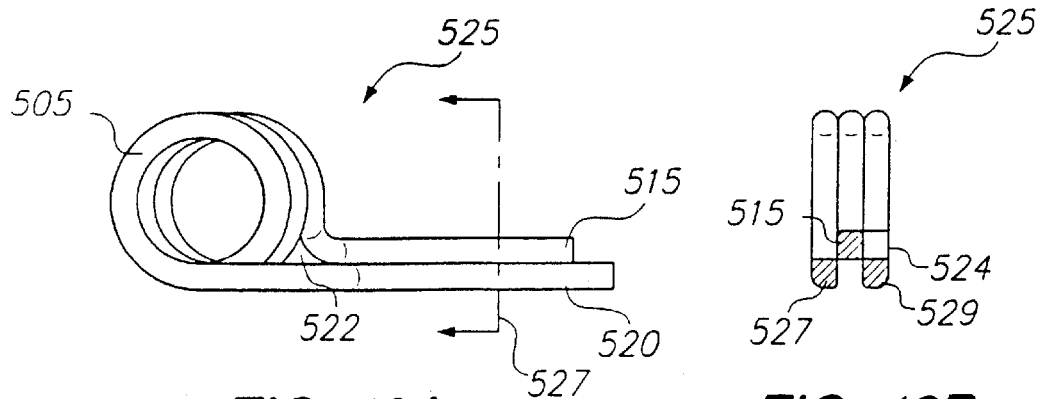
FIG. 16A
FIG. 16B

SURGICAL CLIPS AND APPARATUS AND METHOD FOR CLIP PLACEMENT

RELATED APPLICATION

This application is a continuation of application Ser. No. 09/226,662, entitled "Surgical Clips and Apparatus and Method for Clip Placement", filed on Jan. 8, 1999, by Charles S. Taylor et al. now U.S. Pat. No. 6,193,732.

FIELD OF THE INVENTION

The present invention relates generally to surgical instruments, and more particularly to surgical clips and instruments for applying or placing such surgical clips.

BACKGROUND OF THE INVENTION

A wide number of surgical procedures employ surgical clips of a variety of configurations to provide, for example, hemostasis and occlusion of anatomical structures (i.e., tissue, blood vessels or other fluid ducts) or to secure the ends of a suture, as in place of a conventional suture knot. Often it is required to efficiently place a number of surgical clips during a single surgical procedure.

Surgical clips are commonly used to ligate, clamp, close off or otherwise occlude blood vessels in a surgical site to keep the surgical site free of blood and minimize blood loss from the patient. For example, when the surgery involves the removal of a portion of the body, such as an organ, graft vessel, tumor, or the like, that portion must be first separated from the attached vessels. In these types of procedures a vessel is ligated by action of one or more surgical clips placed at a desired location and is then severed downstream of the ligated location. In some instances, it may be desirable to place one or more clips at two adjacent locations and then sever the vessel in between the locations of the clips.

The clips are often in the form of thin, narrow, metal or polymeric U-shaped or V-shaped members that are placed over the vessel, tissue or suture material and then forced into a closed positioning using a clip applicator constructed for such purpose. The clips, typically constructed of metal, may be initially open and then permanently deformed into a closed or clamped configuration around the desired blood vessel or other tissue structure using an appropriate clip applicator. Examples of such clips are described in U.S. Pat. Nos. 5,201,746; 4,976,722; 4,844,066; 4,799,481; 4,449,530; and 4,146,130.

In many instances, and particularly when the clip is constructed of a material other than metal, the clip will include a latch feature to ensure that the clip remains closed with sufficient force to provide full and complete hemostasis or occlusion and to ensure that the clip will not loosen or open over time. Such latched clips are described, for example, in U.S. Pat. Nos. 5,160,339; 4,620,541, and 4,579,118.

Clips that have clamping members formed in a normally closed position are also known. Normally closed clips typically have their clamping members biased together by way of the elasticity of the material from which it is constructed. In general, to apply a clip configured in a normally closed position, the clamping members must be forced open by an appropriate clip applicator and then released to its closed position in place over the desired structure to be clamped. Normally closed clips may be formed of a continuous wire having torsion spring or tension coil as described, for example, in U.S. Pat. No. 5,593,414 or may be of a variety of other configurations such as, for example, those described in U.S. Pat. Nos. 5,695,505; 5,601,574; 5,366,458; and 4,957,500.

Whether the clip is configured in a normally closed or normally open configuration, the clip must provide sufficient clamping force to secure the structure being clamped. In the case of ligating blood vessels or the like, the clips must provide sufficient clamping force to fully close the vessel to ensure complete hemostasis. In addition, to prevent leakage or positional migration, the clips must remain tightly closed in their clamped position without any significant loosening or relaxing over time.

These requirements tend to result in the necessity for the clip to deliver a substantial amount of force to the structure to be clamped. In turn, the clip applier apparatuses for applying these clips must proportionally provide sufficiently high forces to either deform the clamp to its closed position or force the clamp to an open position for delivery. As a result, known clip appliers have been characterized by relatively complicated and bulky jaw assemblies designed to generate the high forces required to reliably and permanently apply the clips.

The complication and bulkiness associated with the clip applicators have a number of adverse effects. The added size or bulk of the clip applier adversely affects the ability of the surgeon to view the clip that is about to be applied. In many cases, the clip is almost completely obscured from view by the jaw assembly that is required to open or close the clamp. Further, excessive forces required to open or close the surgical clip must ultimately be delivered by the hand of the surgeon, often in the context of very delicate and precise surgical manipulations.

In endoscopic surgical procedures, where the clips must be delivered and applied to a surgical site through the small diametrical operating space of a relatively long cannula, these deficiencies become even more acute. Excessively large clip applicator mechanisms are inappropriate for endoscopic delivery and tend to adversely affect the endoscopic visibility of the clip placement at the surgical site. Further, in an endoscopic procedure, even small movements at the proximal end of a clip applier device may be greatly magnified at the distal end which is located a relatively large distance away at the surgical site. Accordingly, excessive forces required to apply a surgical clip tend to adversely effect the precision with which a clip may be delivered.

In view of these and other prevalent problems of known clips and clip appliers it would be desirable to have a reliable surgical clip configured for placement using only minimal force. It would be further desirable to have a surgical clip that allows improved visual access to its clamping members during placement and closure around a structure to be clamped. Further, it would be desirable to have a clip applier apparatus that can surgically apply the clips to the desired structure without substantial visual obstruction to the clamping portion of the clip. Most desirably, the clip and clip applier apparatus would operate in conjunction to allow the clip applier to be loaded with a number of clips for sequential delivery of one or more clips at a time.

SUMMARY OF THE INVENTION

The present invention involves a surgical clip for clamping or grasping a target structure and having a pair of opposing clamp arms held together in a normally closed relationship by a connecting member. The clamp arms of the surgical clip may be forced open and conveniently held open for placement over a desired structure. In one aspect of the present invention, the clamp arms are held open by a secondary member or locking mechanism. In that case, the clamp arms are released by displacing the secondary member or actuating the locking mechanism. In another aspect of the present invention, the clamp arms are opened or held open by a clip applicator.

In a preferred embodiment, the surgical clip has a first clamp arm and a second clamp arm, each clamp arm having an associated clamping surface. A connecting portion extends between and connects the clamp arms, biasing the clamping surfaces to a substantially parallel and closed relationship. In the closed position, the clamping surfaces may be in direct contact with each other or may be spaced apart a desired distance. The clamp arms are movable to an open position wherein the clamping surfaces are disposed in an angular relationship.

In one aspect of the present invention, the clamp arms and associated clamping surfaces are held open by a device, member, or mechanism or the like disposed between the clamp arms at a position away from the distal ends of the clamp arms. Preferably, the clamp arms are held open at a proximal location along the length of the clamp arms, most preferably near the apex of the angle between the clamping surfaces.

The clamp arms may have opposing surfaces located near the apex of the angle between the clamping surfaces and adapted to receive a secondary member to hold the clamp arms in the opened position. The opposing surfaces may be relatively short compared to the length of the clamping arms, preferably less than about 25% of the length of the clamp arms. In a preferred embodiment, the opposing surfaces are substantially parallel when the clip is in the opened position and spaced apart a distance of between about 0.01 inches (0.25 mm) to about 0.05 inches (1.27 mm).

In one embodiment of the present invention, a secondary member is disposed between the opposing surfaces to hold or lock the clamp arms in the opened position. The secondary member may be a pin or ring-like element having a cross-sectional dimension selected to substantially match the distance between the opposing surfaces when the clamp arms are in the opened position. The opposing surfaces may further include a detent to cooperate with the secondary member.

In one embodiment, the connecting portion includes an opening with the opposing surfaces terminating proximally within the opening. This arrangement of the opening provides clearance for the secondary member once displaced in the proximal direction from between the opposing surfaces, thus allowing the clamp arms to close. Accordingly, the opening is preferably configured to be at least as large as the cross-section of the secondary member so as to allow the clamp arms to close without obstruction. In one preferred embodiment, the connecting portion has a channel extending across its width to provide further clearance of a secondary member or to facilitate removal of a secondary member. The depth of the channel is preferably about 75% or less of the thickness of the connecting portion.

The connecting portion may have any number of orientations relative to the plane of the clamp arms. The clamp arms and connecting portion may be substantially in a common plane, that is, the surgical clip is relatively flat. In other embodiments, the clamp arms may lie in a plane which is parallel and offset from the plane of the connecting portion.

The present invention also involves a surgical clip assembly for clamping a target structure. The surgical clip assembly generally includes a normally closed surgical clip having clamp arms and a secondary member positioned between the clamp arms holding the clamp arms in an opened position.

In a preferred embodiment, the surgical clip has a pair of opposing clamp arms, each clamp arm having an associated clamping surface, and an connecting portion extending therebetween and biasing the clamping surfaces in a substantially closed relationship for clamping a target structure. The clamp arms are moveable to an open position wherein the clamping surfaces are disposed in an angular relationship. The clamp arms preferably have opposing surfaces near the apex of the angle.

The secondary member is preferably positioned between said opposing surfaces to hold the clamping surfaces in the opened position, preventing the clamping surfaces from returning to the substantially closed relationship. The secondary member may be a pin, a ring-like member, or a substantially closed ring. The cross-section of the secondary member may be generally round or substantially square, in any case having a cross-sectional dimension selected to hold the clamping surfaces in the desired open position. In a preferred embodiment, at least a portion of the secondary member is substantially planar to the plane of the clamp arms.

The present invention also involves a method of applying a surgical clip to a target structure using a clip applicator. The method may preferably include the steps of (a) providing a surgical clip having a pair of opposing clamp arms movable between a normally closed position and an open position for receiving a target structure between the clamp arms; (b) forcing the clamp arms from the normally closed position to the open position; (c) locking the clamp arms in the open position; (d) loading the opened surgical clip into a surgical clip delivery device; (e) positioning the target structure between the opened clamp arms; and (f) unlocking the clamp arms, whereby the clamp arms return to the normally closed clamping position over the target structure.

The present invention also involves a method of applying a surgical clip to a target structure. The method preferably includes the steps of: (a) providing a surgical clip having a pair of opposing clamp arms joined at a proximal end and being moveable between a normally closed clamping position and an open position for receiving the target structure; (b) forcing the clamp arms from the normally closed clamping position to the open position; (c) positioning a secondary member at a proximal position between the opposing clamp arms, the secondary member preventing the clamp arms from returning to the closed position; (d) positioning the target structure between the opened clamp arms; and (e) displacing the secondary member from the proximal position, whereby the opposing clamp arms are allowed to close upon the target structure. The method may further involve the steps of (f) displacing the secondary member to a position within a clearance hole provided immediately proximal to the proximal position of the secondary member; and (g) removing the secondary member from the clearance hole.

In one embodiment, the step of forcing the clamp arms from the normally closed position to the open position comprises the steps of providing a stationary pin at a distal location relative to the clamp arms, moving the surgical clip towards the pin until the pin engages and begins to spread the clamp arms, and advancing the clip relative to the pin until the pin is at the proximal position and the clamp is opened. Preferably, the pin is oriented substantially transverse or perpendicular to the plane of the clamp arms.

The present invention also involves a clip applicator for delivering a surgical clip assembly having a surgical clip and a secondary member holding the surgical clip in an opened position. The secondary member is preferably a pin or ring, at least a portion of which is relatively perpendicular to the plane of the surgical clip. According to one aspect of the present invention, the clip applicator holds the secondary member in a fixed position and urges or advances the surgical clip relative to the secondary member to displace the surgical clip from the secondary member, thus allowing the surgical clip to close.

In one embodiment, the clip applicator has a shaft member having a distal slot for receiving the body of the clip and one or more additional features (i.e., hooks, slots, etc.) for holding or capturing the secondary member, which preferably is positioned at a proximal position between the clamp arms; The shaft member may have a slidable rod disposed within a central lumen, the distal end of the rod adapted to engage the surgical clip and urge it in a distal direction to displace it from the secondary member. The secondary member may be a pin or ring or the like having a cross-sectional dimension selected to hold the surgical clip in the desired open condition.

The present invention also involves a clip applicator for delivering a surgical clip to having an elastic connecting portion which, when compressed, opens the clamp arms. The clip applicator generally has a delivery tube having a central lumen for receiving one or more surgical clips. At least a portion of the central lumen is sized and dimensioned to hold the connecting portion in a compressed state, thereby holding the clamp arms in an open position. When the connecting portion of the surgical clip is advanced beyond the distal end of the central lumen, the connecting portion is allowed to return to its uncompressed state, thus closing the clamp arms. A number of surgical clips may be sequentially advanced through the central lumen.

Common to the various embodiments of the present invention just described is the ability to actuate a surgical clip over a target structure without excessive mechanism in the area of the clamp arms, thus optimizing visual access during a surgical procedure. The surgical clips of the present invention are actuated by features located proximal to the clamping area of the surgical clip clamp arms, allowing the use of mechanisms that are greatly simplified. These and other advantages of the present invention will become apparent from the following detailed description and accompanying drawings.

BRIEF DESCRIPTION OF THE DRAWINGS

FIG. 1A shows the surgical clip in an intermediate open condition. FIGS. 1B and 1C show the surgical clip in a final closed position and an open position respectively.

FIGS. 6A, 6B, and 6C are front views of a surgical clip in an intermediate open position, a final closed position, and an operative open position respectively.

FIGS. 7A, 7B, and 7C are front views of a surgical clip having longitudinal clamp features in an intermediate open position, a final closed position, and an operative open position respectively.

FIG. 7D is a cross-sectional view along lines 7D—7D as shown in FIG. 7B.

FIG. 7E is a cross-sectional view showing an alternate configuration of the longitudinal clamp features of the surgical clip of FIGS. 7A–7C.

FIGS. 11A and 11B are front and end views, respectively, of an exemplar wire surgical clip constructed according to the principles of the present invention.

FIGS. 12A and 12B are front and end views, respectively, of an alternate construction of a wire surgical clip.

FIGS. 13A and 13B are front and end views, respectively, of another wire surgical clip.

FIGS. 14A, 14B and 14C are perspective, frond and end views, respectively, of a coiled wire surgical clip.

FIGS. 15A and 15B are front and end views, respectively, of an alternate construction of a coiled wire surgical clip.

FIGS. 16A and 16B are front and end views, respectively, of an alternate construction of a coiled wire surgical clip.

DETAILED DESCRIPTION

The present invention involves a surgical clip, a clip applying apparatus, and a method of applying a normally closed surgical clip. The present invention generally involves surgical clips having a pair of opposing clamp arms held together in a normally closed relationship by a connecting member. The clamp arms of the surgical clip may be forced into an operative open condition and locked or otherwise held for placement over a desired structure.

The particular constructions of the surgical clips and clip applicators, as described in detail below, require only very simple mechanism for their actuation. Whereas prior art devices typically require a clip applicator having a jaw mechanism capable of providing a substantial closing force (if the surgical clip is normally open) or a substantial separating force (if the surgical clip is normally closed) to the clamping arms of the surgical clip, the surgical clips of the present invention are constructed to require only minimal force for surgical placement.

In one aspect of the present invention, the normally closed surgical clip may be pre-loaded into an operative open position prior to installing the clip on an applicator. The surgical clip may be held in the open position by a locking device or a secondary member. The clip may then be released to a final closed position over a target structure by releasing the locking device or by displacing the secondary member. In this way, substantial loading forces can be used, for example at a manufacturing facility, to open the surgical clip and thereafter the clip applicator mechanism is required only to supply a force sufficient to actuate or displace the locking device or secondary member. In a preferred embodiment, the clip may be released by application of an axial force directed substantially along the axis of the delivery shaft.

The present invention also involves surgical clip applicators for delivering and actuating surgical clips upon a target structure. The surgical clips of the present invention allow clip applicators to have a greatly simplified construction and minimized overall size and profile. Since the forces required for clip actuation are significantly reduced, there is no need to include complicated mechanisms to gain mechanical advantage. Of particular advantage, the clip applicators of the present invention do not require any mechanism in the area of the clamping members of the surgical clip. Thus the surgical clip and the structure which is to receive the surgical clip can remain in full view of the surgeon and increased precision enabled during actuation because of the lowered forces involved with releasing the clip.

Figure 1A:
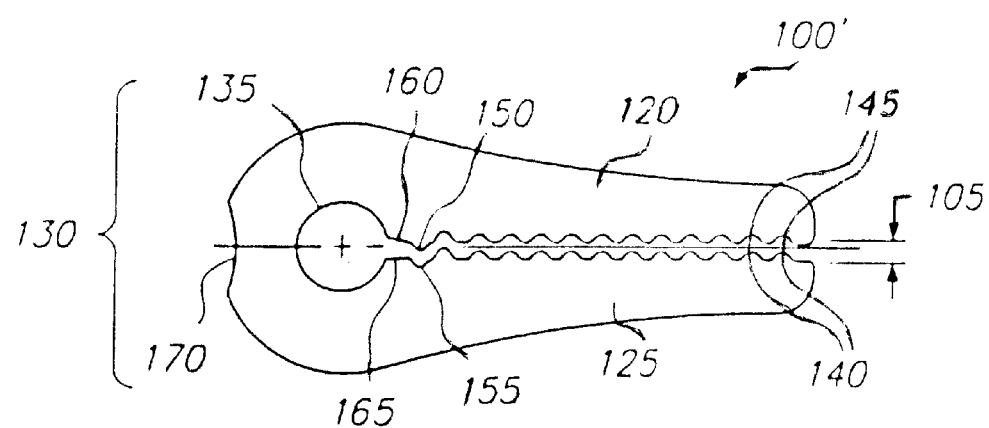
FIGS. 1A, 1B, and 1C are front views of a surgical clip made according to the principles of the present invention.
Figure 1B:
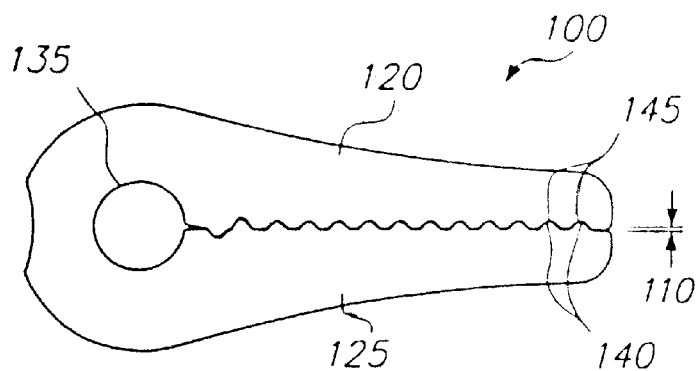
Figure 1C:
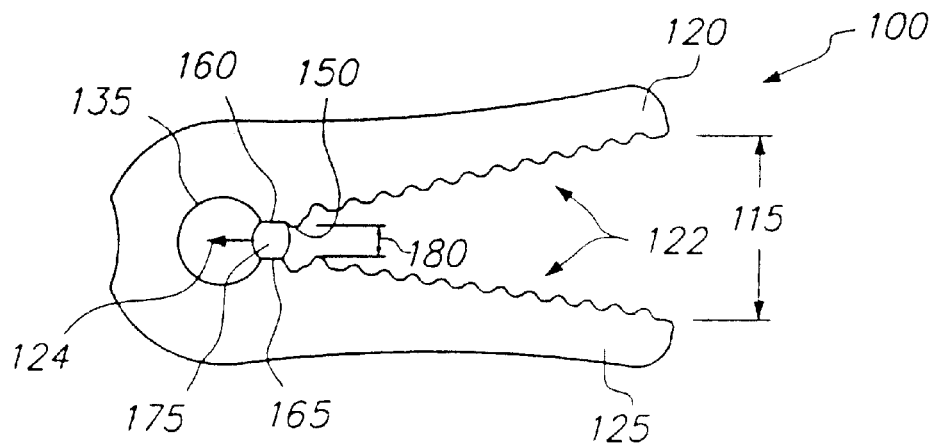

In one embodiment of the present invention, the surgical clip has a relatively flat configuration, preferably made from a flat sheet material. A preferred clip constructed in accordance with the principles of the present invention is shown in FIGS. 1A–1C. Surgical clip 100 has a first clamping member 120, an opposing clamping member 125, and a connecting portion 130. As will be described in more detail below, the surgical clip may be manufactured having an optional intermediate shape as shown in FIG. 1A, and then formed into a final, normally closed shape as shown in FIG. 1B. The clip has one or more open positions, where the opposing clamp members 120 and 125 are opened an amount sufficient to accept a target structure to be clamped as shown in FIG. 1C.

Clamping members 120 and 125 are generally constructed to have gripping features along their inner surfaces selected to optimize their gripping or clamping function on the intended structure. When the surgical clamp is to be used as a hemostatic or ligating clamp on blood vessels or other tissue structures within the body, the gripping features will generally be in the form of serrations or teeth or the like disposed in the clamping region of clamp arms 120 and 125. In the preferred embodiment shown, clamp member 125 has one or more transverse raised features, peaks, or teeth 140 positioned to correspond with recessed features or valleys 145 in opposing clamp member 120.

In the final closed position (FIG. 1B), the gripping features or teeth of clamp arms 120 and 125 may be biased against each other in full or partial contact or may be preferably positioned in a very closely spaced relationship. The spacing 110 between the mating features on the opposing clamp members 120 and 125 may range from essentially zero to as large as required to guarantee effective clamping without damaging the clamped structure. In the case of ligating blood vessels or the like, providing a spacing between the opposing clamping arms which is too big will result in incomplete hemostasis. If the spacing is too small, the vessel may disadvantageously shear and separate from the surgical clip. Preferably, the final spacing 110 between the opposing clamp arms is selected to be about 20% to about 90% of the collapsed thickness of the vessel to be clamped. For example, in the specific application of clamping or ligating the small branch vessels extending from internal mammary artery or saphenous vein, spacing 110 is in the range from about 0.0 inches (0.0 mm) to about 0.003 inches (0.076 mm), most preferably about 0.001 inches (0.025 mm).

The shape and features of the surgical clip can be produced using any manufacturing process suitable for the particular size, geometry, and material of the desired surgical clip. For example, starting with flat stock material, the desired features and geometry of the surgical clip can be produced by milling, stamping, fine blanking, chemical machining, abrasive jet machining, wire electrical discharge machining (EDM), or other like process. The surgical clips may also be molded, cast or extruded and cut to the desired thickness or final shape. The surgical clips may be made of any suitable medical grade material including, but not limited to, polymers having sufficient resiliency, stainless steel, tantalum, titanium, and memory metals having super-elastic characteristics.

Depending on the complexity of the clip geometry and the manufacturing process used to produce the clip, it may be desirable to manufacture the surgical clip first in an intermediate shape and then secondarily form the final shape. In a preferred embodiment, an intermediate shape shown as 100' in FIG. 1A allows the fine details of the surgical clip (i.e., the teeth in the clamp members) to be conveniently cut or otherwise manufactured with the clamp arms spaced apart a greater distance than the final desired configuration.

The spacing 105 in the intermediate configuration may be selected to be large enough to allow efficient passage of an appropriate cutting, milling, wire-EDM, or like tool. Spacing 105 is preferably selected to be at least as large as the cut produced by the cutting tool. When spacing 105 is selected to be the same as the width of the cut produced by the cutting tool, it is possible to create the internal features on clamping arms 120 and 125 using a single tool path. For example, in a wire-EDM process employing a wire electrode, spacing 105 is preferably selected to be equal or greater than the width of the minimum slot width that can be cut by the wire electrode (typically there is a certain amount of over-cut beyond the diameter of the wire electrode itself).

When an intermediate shape or configuration is employed to facilitate formation of the geometry of the surgical clip, a secondary operation will usually be required to obtain the final desired shape or configuration. In a preferred embodiment, the surgical clip is made from a metal material which allows the intermediate clip 100' to be forced into the final shape and then heat treated.

Preferably, a shape memory alloy such as Nitinol™ is used for the surgical clip material. In that case, intermediate shape 100' placed into and held in the desired final condition, and heat treated in that constrained condition at a temperature in the range of about 450° C. to about 550° C. for a time of about 20 minutes to about 1 hour. More preferably, the clip is heat treated in the constrained condition at a temperature in the range of about 530° C. to about 560° C. for about 30 minutes to about 45 minutes. After heat treating the clip is preferably quenched with water or other suitable fluid.

As described above, clip 100 may have clamp arms 120 and 125 biased against each other with some predetermined residual force. That is, clamp arms 120 and 125 will always apply at least a minimum amount of force applied to the clamped structure regardless of the compressed size of the structure.

For delicate tissue structures, however, it may be desirable for clamp arms 120 and 125 to maintain a predetermined spacing 110 as described above. In this configuration, clamp arms 120 and 125 do not have any biasing force at the resting, normally closed position. The elasticity of the clip material, and in particular connecting portion 130, resist separation of the clamp arms from their resting position. The amount of force delivered by the clamp arms is generally a function of the geometry and elastic modulus of the clip and is in proportion to the distance the clamp arms are displaced from their resting position (generally in accordance with well known theories of elasticity of materials). Thus, within the elastic limits of the clip material, clamp arms 120 and 125 exert the greatest clamping force at their widest open position; the clamping force decreasing to zero at the resting position. This construction greatly reduces the likelihood of over-compression, shearing, or other such damage to the clamped structure.

Connecting portion 130 generally joins the clamp arms at their proximal end and acts in the manner of an elastic hinge that allows the clamp arms to deflect open and elastically return closed. In addition to certain functional considerations (i.e., manufacturability, features for efficient surgical clip placement, etc.), the size, shape, and orientation of the connecting portion 130 is selected to provide the desired forces at the clamping arms without exceeding acceptable stress or strain limits of the material. In to general, for a given material, connecting portions having an increased cross-section will result in higher forces as the clamp arms are displaced. Conversely, the cross-section of a connecting portion may be reduced by removing material from connecting portion 130 to reduce the forces required to displace the clamping arms. A region of reduced material or cross-section may be created in connecting portion 130 by way of a cutout or notch 170 as shown.

From the final closed position shown in FIG. 1B, clamp arms 120 and 125 may be displaced outwardly to an operative open position as shown in FIG. 1C. In the open position, clamp arms 120 and 125 are generally displaced at an angle, the apex of which being proximal to clamping region of the clamp arms. The open position of clamp arms 120 and 125 is preferably large enough to accept the structure to be clamped in its substantially uncompressed or natural state. Accordingly, the distal spacing 115 between clamp arms 120 and 125 is preferably larger than the profile of the structure to which the clip is to be applied.

Clip 100 may be manipulated to and held in an operative open position by an appropriately constructed clip applicator at the time of use or clip 100 may be pre-opened and locked or held in an opened position until released in use. In one embodiment, clip 100 may be manipulated to an open position and locked open by way of a locking feature. The locking feature may be of a wide range of constructions including, but not limited to, a deflecting, deformable, or otherwise articulating projection extending from one or both of the clamp arms or a secondary member positioned in any manner which prevents clamp arms 120 and 125 from returning to their closed positions. Preferably, the locking feature is positioned at a proximal position relative to the clamping region of the clamp arms. Most preferably, the locking feature is positioned at or near the apex of the angle formed by the clamping surfaces of the clamp arms.

According to one embodiment of the present invention, clip 100 is manipulated to an open position and locked in place by a secondary member, such as pin 175. Clip 100 may be opened, for example, by placing clip 100 in a fixture and forcing the clamp arms open using an angled wedge or other suitable tool. When the clip is constructed of a material having shape memory characteristics, the clamp arms may be completely or partially opened by cooling the surgical clip to a temperature below the transition temperature of the shape-memory alloy. Once opened, pin 175 is placed between the clamp arms, preferably at or near the apex of the included angle formed by the respective inner clamp surfaces or regions 122 of clamp arms 120 and 125. Pin 175 may be of any convenient cross-sectional shape having an outer dimension 180 selected to hold clamp members 120 and 125 in an open condition with the desired operative distal opening 115.

Clip 100 may desirably include features to positively hold the secondary member in place. In a preferred embodiment, inner clamp regions 122 of clamp arms 120 and 125 have opposite holding features in the form of first surface 160 and second surface 165. First and second surfaces 160 and 165 are preferably facing each other in an opposing relationship. In a preferred embodiment, first and second surfaces 160 and 165 are substantially flat or planar. When clip 100 is in the opened position, first and second surfaces 160 and 165 are preferably substantially parallel relative to each other and preferably have a spacing therebetween corresponding to the cross-sectional dimension of the secondary member. In a preferred embodiment, the spacing between first and second surfaces 160 and 165 will be in the range of about 0.01 inches (0.25 mm) to about 0.125 inches (3.175 mm), more preferably from about 0.01 inches (0.25 mm) to about 0.05 inches (1.27 mm). Pin 175 may optionally include mating surfaces corresponding to first and second surfaces 160 and 165.

In use, clip 100 is released or closed simply by displacing pin 175 in any manner which allows clamp arms 120 and 125 to close on its intended structure. Pin 175 may be displaced in a direction perpendicular to the plane of the clip. More preferably, pin 175 is displaced in the direction of arrow 124 relative to clip 100. This may be accomplished by holding clip 100 stationary and displacing pin 175 in the direction indicated by arrow 124, by holding pin 175 stationary and pushing clip 100 in a direction opposite to arrow 124, or any combination of the two.

Preferably, first and second surfaces 160 and 165 lead proximally into a central opening 135 sized to provide sufficient clearance for pin 175 to be removed once displaced from first and second surfaces 160 and 165. A raised feature 150 may be employed distal to first and second surfaces 160 and 165 to ensure that pin 175 is placed at the proper location and to prevent pin 175 from being accidentally displaced into the clamping region of clamp arms 120 and 125. So that raised feature 150 does not inhibit proper closing, the arm opposite raised feature 150 has a clearance recess 155.

The amount of force required to displace pin 175 is primarily a function of the closing forces of the clip, the coefficient of friction between the clip material and pin 175, and the geometry of the holding features of the surgical clip. For illustration purposes only, first and second surfaces 160 and 165 have been shown and described as being substantially flat and parallel, however a wide variety of holding features may be employed to adjust or tailor the amount of force required to displace the locking feature, in this case pin 175. For example, to reduce the amount of force required to displace pin 175, first and second surfaces 160 and 165 could be angled and diverging proximally. To increase the amount of force required to displace pin 175, first and second surfaces 160 and 165 may be angled, converging proximally. In addition, the holding features may involve concave or convex curved surfaces or employ a detent or the like to optimize the displacement characteristics of a particular locking feature.

In one variation, the holding features may be a part of or associated with the central opening 135. Surgical clip 100 may be manipulated to an open position and locked open by placing an appropriately sized secondary member (not shown) within central opening 135. Further, a tapered secondary member (i.e., a cylindrical pin having a tapered end portion) may be drawn into central opening 135 in a direction transverse to the plane of the surgical clip, the tapered end portion forcing clamp arms 120 and 125 to an open position. Further advancement of the tapered secondary member in the transverse direction dislodges the secondary member from central opening 135, thus allowing clamp arms 120 and 125 to return to their normally closed position.

A surgical clip locked into an open position by a displaceable locking feature may then be conveniently delivered surgically using greatly simplified clip applicators. Since the clip has already been forced open and locked, no complicated mechanism is required to force open the clamping arms of the surgical clip. All that is required to release the clamping energy stored within the natural elasticity of the clip material is to displace the locking feature, which as described above may be constructed to require only a relatively small displacing force. Further, since the locking feature is advantageously positioned at a proximal position, i.e., towards the apex of the clamping arms, the clamping arms may be kept free from any associated mechanism that would tend to obstruct the clear view of the clamp arms and the structure to be clamped.

Figure 2:
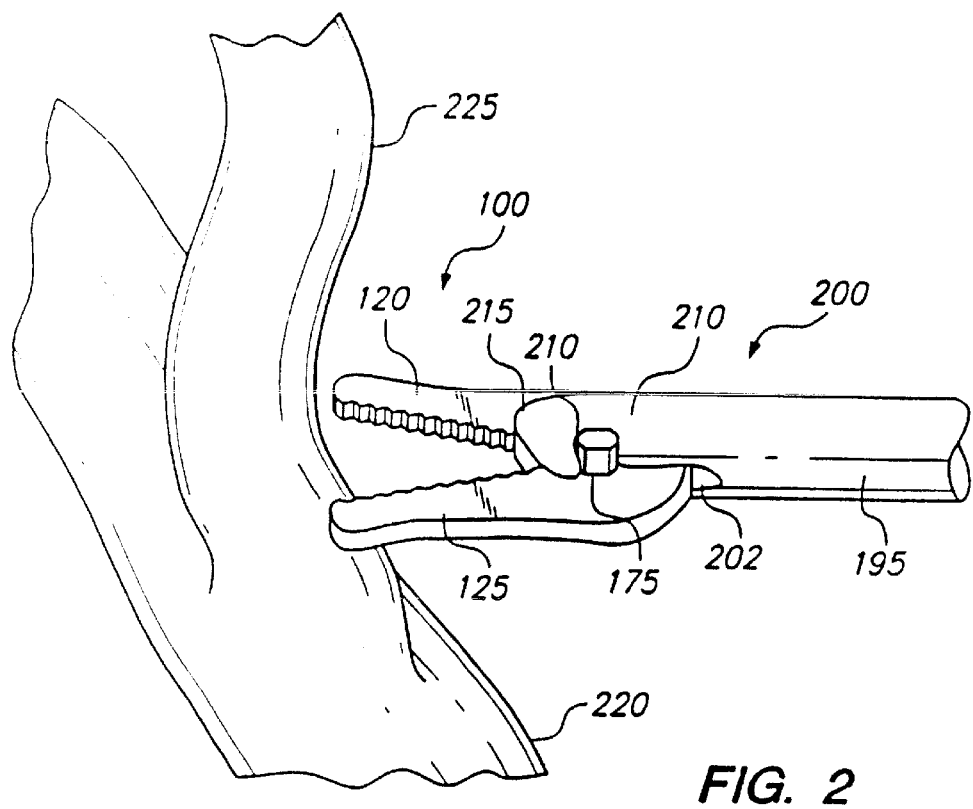
FIG. 2 is a perspective view of an open surgical clip installed on a clip applicator.
Figure 3:
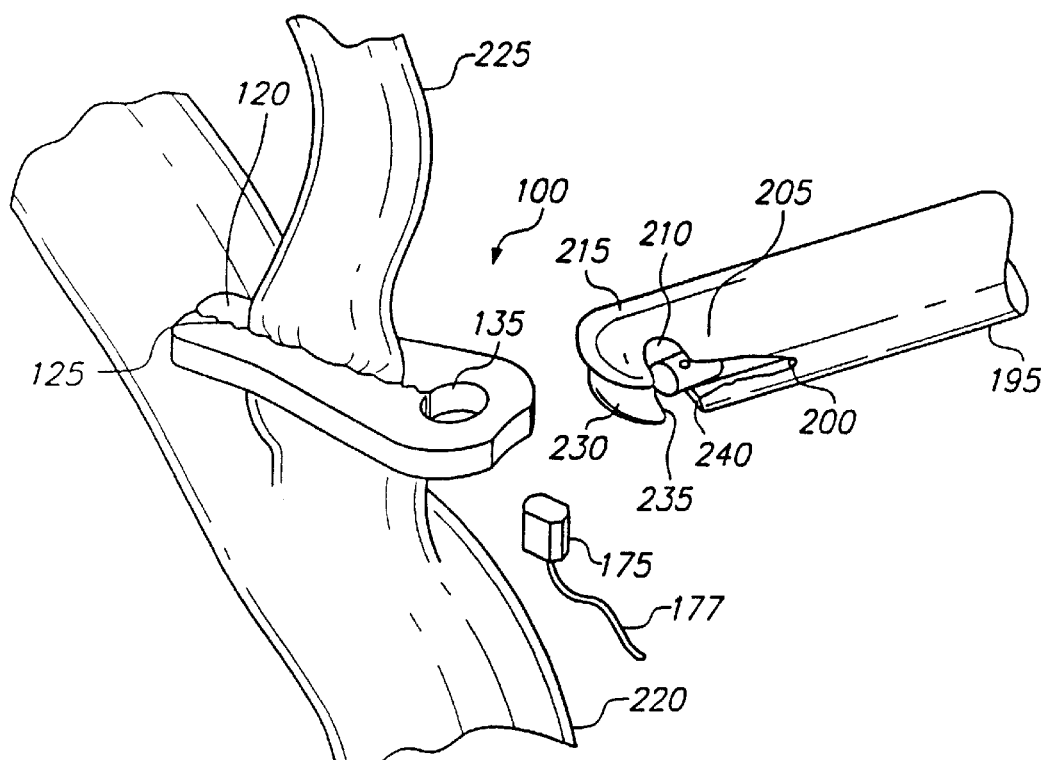
FIG. 3 is a perspective view illustrating a surgical clip after release from a clip applicator.
Figure 4:
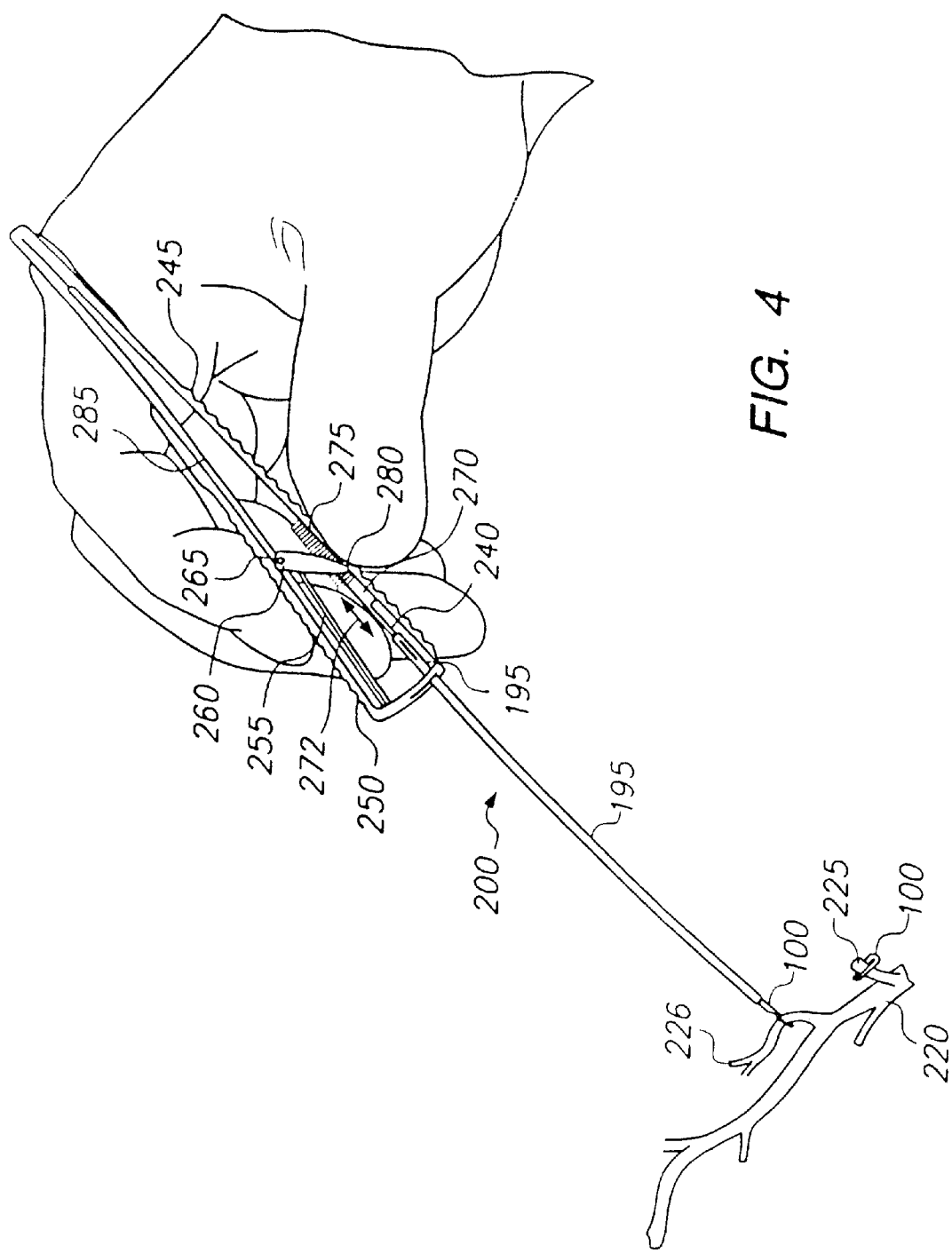
FIG. 4 is a perspective view illustrating an exemplar clip applicator constructed in accordance with the principles of the present invention.

The surgical placement of surgical clip 100 by a suitable clip applicator is shown with reference to FIGS. 2–4. FIG. 2 shows a perspective view of surgical clip 100 loaded into place on the distal end of clip applicator 200. With surgical clip 100 held in the open position by operation of a locking member or secondary member, clamp arms 120 and 125 can be positioned over a structure to be clamped. The locking member or secondary member may then be actuated or displaced to release surgical clip 100 to its normally closed position, thus securing the structure. Although the clip and clip applicator of the present invention may be useful in a wide range of surgical applications involving both tissue structures and various suture materials, the examples that follow will be described primarily with reference to the specific example of ligating a vessel, such as branch vessel 225 extending from truck vessel 220.

In a preferred embodiment, clip applicator 200 has a tubular shaft 195 terminating in a distal instrument tip 205. Instrument tip 205 preferably has a distal slot 202 for receiving clip 100. In the embodiment shown, distal slot 202 bifurcates instrument tip 205 into first and second sides 215 and 230, each having a respective slot 210 and 235 for receiving and holding the ends of pin 175. To keep pin 175 engaged within slots 210 and 235 during positioning and placement of clip 100, pushrod 240 may be employed to push slightly on the proximal end of clip 100. To return clip 100 to its closed position, pushrod 240 pushes on the proximal end of clip 100 with sufficient force to urge clip 100 forward, displacing it from pin 175 (which is held in place within slots 210 and 235).

Clip applicator 200 will generally employ a suitable mechanism at the proximal end of the shaft 195 for activating pushrod 240. The exact form of the mechanism will be determined according to the particular ergonomic requirements of the proposed surgical procedure to allow the surgeon the greatest comfort, efficiency and precision. Pushrod 240 may be actuated by way of a pistol grip type actuator, a sliding or rotating button or lever, or driven by an electric or hydraulic solenoid. In many instances, it will be desirable for the actuator to be in the same form as other conventional instruments that are used in the particular type of surgery in which the clip is to be used.

In one example, the actuator for pushrod 240 is designed to be held in one hand in a manner similar to conventional forceps. The actuator mechanism of clip applicator 200 includes a pair of proximally hinged handle members 245 and 250, similar in design to conventional surgical forceps. Shaft 195, having an internal lumen for slidably receiving pushrod 240, is attached to the inside of handle member 245. Pushrod 240 extends proximally from shaft 195, terminating at proximal end 285 which is preferably constrained in a lengthwise slot in handle member 245. Connected to pushrod 240 is slider 270 which may be constrained by way of a rail or the like (not shown) to slide relative to handle member 245 in the direction of arrow 272. Pivoting link 260 is connected to handle member 250 at hinge or pivot pin 265. Pivoting link 260 has free end 280 which butts against the proximal end of slider 270 as shown. Pivoting link 260 is biased in a counter-clockwise direction by way of cantilever spring 255, which is preferably a flexible wire or the like.

Preferably, a compression spring 275 is positioned over pushrod 240 proximal of slider 270 to bias slider 270 (and pushrod 240) in the distal direction. With clip 100 loaded into the features at the distal end of shaft 195 as described above, compression spring 275 preferably delivers enough force to bias the distal end of pushrod 240 against clip 100 to hold pin 175 within slots 210 and 235. The clamp arms may then be positioned over the structure to be clamped.

To actuate the clip applicator, handle members 245 and 250 are articulated towards each other in a manner similar to conventional forceps. As handle members 245 and 250 close together, free end 280 of link 260 urges slider 270 and attached pushrod 240 in a distal direction. The distal end of pushrod 240 pushes against pin 175, causing pin 175 to be dislodged from the clip and allowing the clip to close about the intended structure as shown in FIG. 3.

After pin 175 is dislodged, it is loose within central opening 135, and may be removed by any convenient means. With the pin removed, clip 100 is completely freed from the clip applicator. It may be desirable to optionally attach one end of tether 177 or the like to pin 175. The other end of tether 177 may be attached to a large marker, or may be attached by way of a removable band to the outside diameter of shaft 195.

Figure 5A:
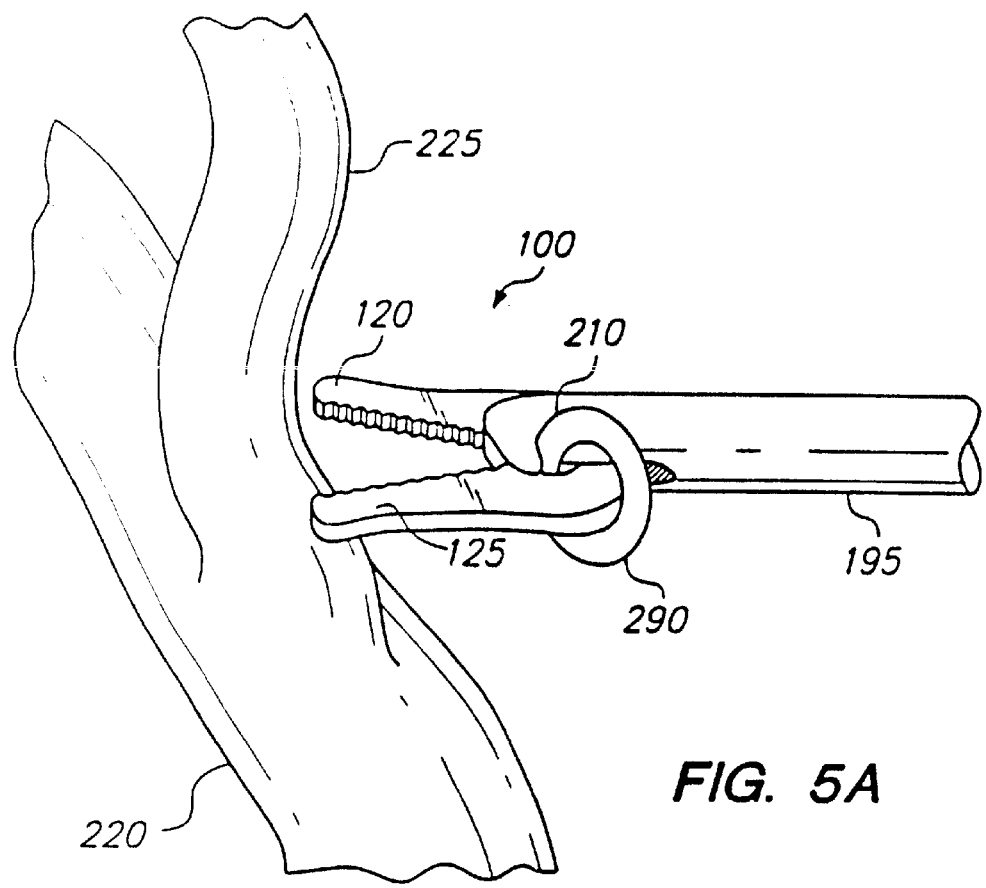
FIG. 5A is a perspective view illustrating an open surgical clip installed on a clip applicator.

In another embodiment, a locking member or other secondary member that remains permanently attached to clip 100 may be used. For example, clip 100 may be held in an open position by a portion of a substantially closed member, such as ring 290 as shown in FIG. 5. As ring 290 becomes displaced into central opening 135, and clip 100 closes, ring 290 becomes permanently captured and remains attached through central opening 135.

A clip having a locking mechanism or secondary member adapted to hold the clip in an open position as described herein allows the surgical clip to be easily adapted to a wide range of simplified clip applicators and surgical situations. For example, since the surgical clip needs only to be displaced from the secondary member (or vice versa), the clip applicator may advantageously use a simple cam mechanism to provide the displacing motion. In addition, the surgical clip could easily be delivered at any desired angle relative to the delivery shaft. Such configurations are facilitated to a large extent by the simple, low-force, motion required to actuate the surgical clip to the closed position.

Figure 5B:
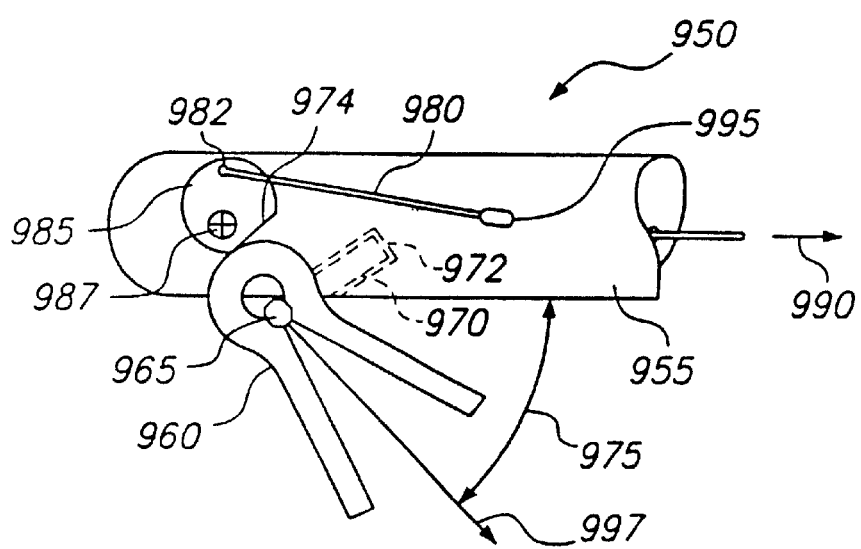
FIG. 5B is a top view illustrating an open surgical clip installed at an angle relative to a cam actuating clip applicator.

FIG. 5B illustrates a clip applicator having a cam actuator for delivering a surgical clip at an angle relative to the clip applicator. Clip applicator 950 has a distal delivery shaft 955 having a cam 985 attached to delivery shaft 955 to pivot about pivot pin 987. Cam 985 is rotated about pivot pin 987 by way of linkage or cable 980 attached to cam 985 at position 982 which is radially offset from pivot pin 987. The linkage or cable 980 may be routed through guide lumen 995 within delivery shaft 955. Normally closed surgical clip 960 is held open by secondary member 965. Secondary member 965 preferably has angled portion 970 which is received into a mounting recess 972 or the like in delivery shaft 955. Angled portion 970 may be held into place by friction against the interior of mounting recess 972 or angled portion 970 and recess 972 may include mating features to lock angled portion 970 into place within recess 972. The angle 975 between the centerline of the surgical clip and the delivery shaft can be any desired angle between 0° and 180°. The surgical clip is actuated to its closed position by urging linkage or cable 980 in the direction of arrow 990 to turn cam 985 such that cam surface 974 urges surgical clip 960 relative to secondary member 965 in the direction of arrow 997.

Surgical clip 100 can be manufactured to have a wide range of sizes; the exact size and configuration depending upon the intended use and the size and nature of the structure desired to be clamped. For example, surgical clip 100 may have an overall length ranging from about 0.125 inches (3.175 mm) to about 0.75 inches (19.05 mm) or more and a thickness in the range from about 0.005 inches (0.127 mm) to about 0.05 inches (1.27 mm). Surgical clip 100 adapted for use in ligating small blood vessels, such as the branch vessels extending from the internal mammary artery (IMA) or the saphenous vein, will typically have an overall length in the range from about 0.25 inches (6.35 mm) to about 0.35 inches (8.89 mm) and a thickness of about 0.01 inches (0.25 mm) to about 0.02 inches (0.51 mm).

Exemplar dimensions for a preferred surgical clip of the type shown in FIGS. 1A–1C, configured for ligating the branch vessels of the IMA or saphenous vein may include a length of about 0.3 inches (7.62 mm) and a thickness of about 0.015 inches (0.381 mm). The length of the clamp arms 120 and 125 may be about 0.20 inches (5.08 mm). The diameter of the central opening may be about 0.045 inches (1.143 mm). Outer dimension 180 of the locking member may be on the order of about 0.018 inches (0.457 mm), resulting in an open spacing 115 of about 0.10 inches (2.54 mm). The spacing 110 between the clamp arms in the closed position is about 0.001 inches (0.025 mm). Of course, one skilled in the art will recognize that a number of other dimension can be used to obtain a wide range of desired functional characteristics.

The type of surgical clips described above can be easily constructed to have a wide range of configurations. FIGS. 6A–9C illustrate a number of alternate surgical clip constructions in accordance with the principles of the present invention. In each case, the surgical clip is preferably formed from a generally flat material having a pair of opposing clamp arms configured in a normally closed relationship as discussed above. To facilitate improved manufacturability, an intermediate shape may be used.

Preferably, the surgical clips are configured to allow the clamp arms to be opened, and then locked into the open position for subsequent surgical placement. In one embodiment, this is accomplished by way of a locking feature or secondary member positioned at or in proximity to the apex of the clamp arms so that the clamp arms remain substantially unobstructed by undesirable mechanisms. Of course, one of ordinary skill in the art will recognize that any feature or principle discussed with reference to a particular figure will be equally applicable to the various other clip constructions described with reference to the other Figures shown and described herein.

FIGS. 6A–6C show surgical clip 300 having opposing clamp arms 305 and 310 connected by connecting portion 315. As discussed above, the relevant attributes of connecting portion 315 are selected to provide the desired elastic clamping force to opposing clamp arms 305 and 310. In this embodiment, clamp arms 305 and 310 have directional transverse clamp features. That is, clamp arm 310 has only upwardly extending raised features such as teeth 320, and clamp arm 305 has a plurality of corresponding recesses 325.

FIGS. 7A–7E show surgical clip 330 with opposing clamp arms 305 and 310 having longitudinal clamp features 335 and 340. In a preferred embodiment, longitudinal clamp features 335 and 340 are recessed grooves or channels extending along at least a portion of the length of each respective clamp arm 305 and 310 as shown in cross-section in FIG. 7D. Recessed channels 335 and 340 tend to be less traumatic to the clamped structure and tend to reduce the likelihood of shearing during clamping. In some instances, for example when clamping sutures or the like, it may be desirable for the longitudinal features to form a more tortured path to maximize the ability of the clamp arms to prevent relative slippage of the clamped structure. In one embodiment, this may be accomplished by providing raised longitudinal tooth 355 on clamp arm 305 and corresponding recessed channel 345 on opposing clamp arm 310.

Figures 8A, 8B:
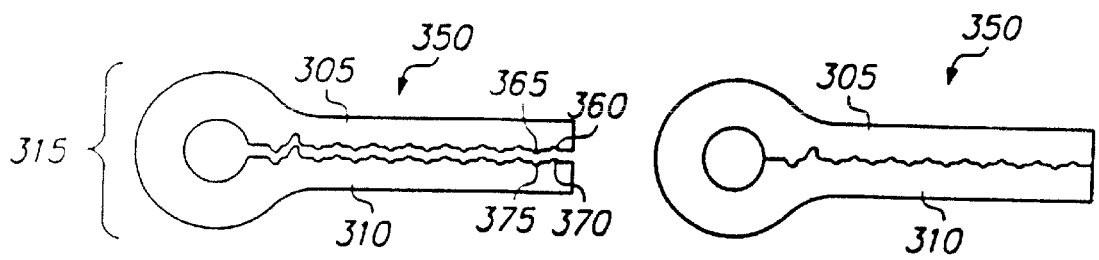
FIGS. 8A, 8B, and 8C are front views of a surgical clip in an intermediate open position, a final closed position, and an operative open position respectively.
Figure 8C:
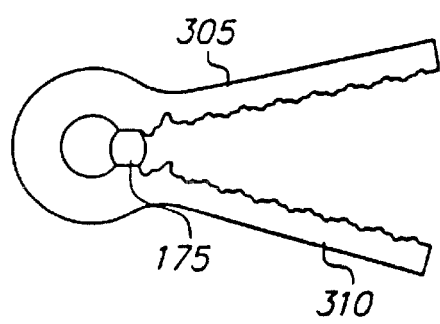

FIGS. 8A–8C show surgical clip 350 with clamp arms 305 and 310 having alternating transverse clamping features. Clamp arm 305 has an alternating series of raised features or teeth 365 and recesses 360. Clamp arm 310 includes alternating recesses 375 and teeth 370 aligned to mate with teeth 365 and recesses 360, respectively, on opposing clamp arm 305.

Figures 9A, 9B:
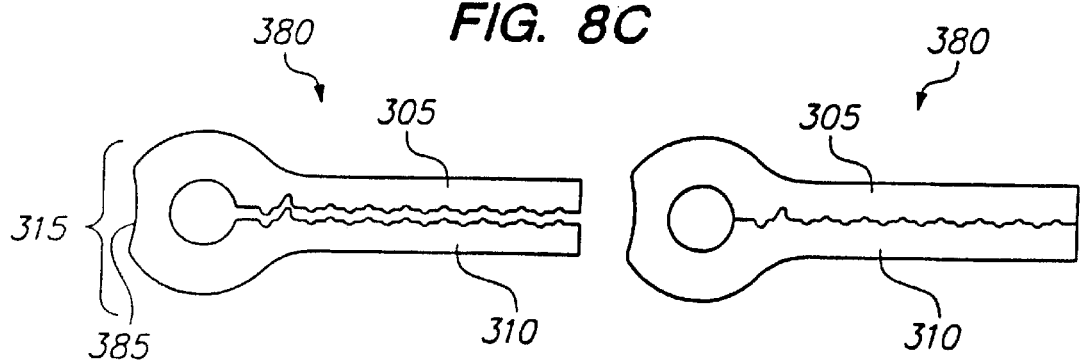
FIGS. 9A, 9B, and 9C are front views of a surgical clip in an intermediate open position, a final closed position, and an operative open position respectively.
Figure 9C:
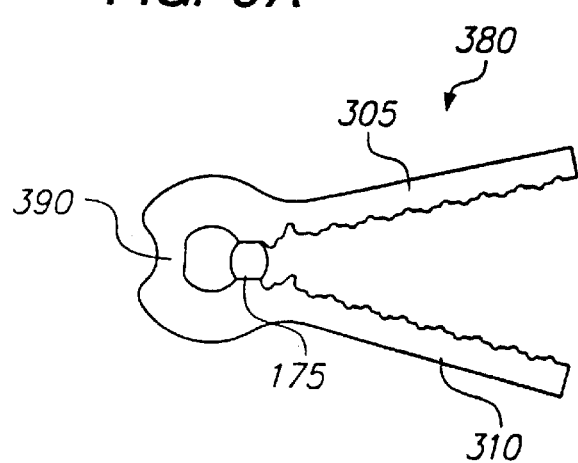

Surgical clip 380, shown in FIGS. 9A–9C, is similar to surgical clip 350 except that clamp arms 305 and 310 and connecting portion 315 have been configured to provide a somewhat lower force at the clamp arms (for a given material thickness). In particular, connecting portion 315 has a region of reduced bulk or cross-section 390. In a preferred embodiment, an area of reduced cross-section is achieved by way of a relief or notch 385 which removes material at the proximal end of clip 380. The region of reduced bulk or cross-section 390 tends to allow an increased amount of deformation for the same amount of force. Thus, opposing clamp arms 305 and 310 may be opened with a reduced amount of force.

Although the embodiments described above have been discussed with reference to a generally flat material construction other constructions may be used to obtain the advantageous features of the present invention. For example, the principles of the present invention may be carried out using wire or like constructions. In one embodiment, a normally closed surgical clip may have clamp arms of any convenient material connected to an elastic connecting portion conveniently formed of a surgical grade wire material. In another embodiment, the entire surgical clip may be formed from a wire material.

Figure 10A:
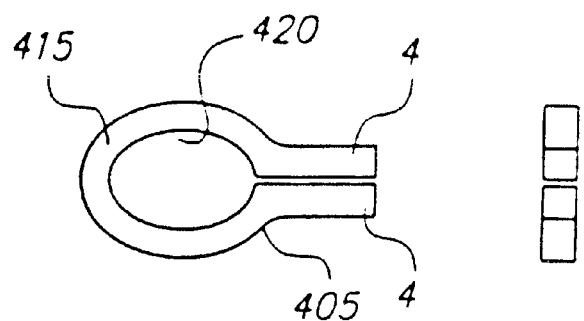
FIG. 10A is a front view of a surgical clip base made according to the principles of the present invention.
Figure 10B:
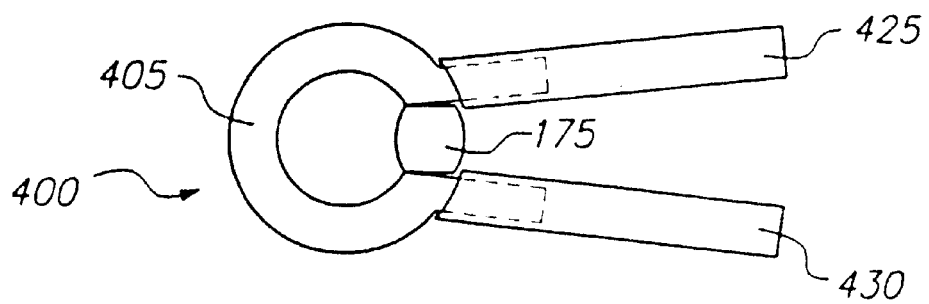
FIGS. 10B and 10C are front views showing the surgical clip base of FIG. 10A supported in an operative open position having straight and profiled clamp arms respectively.

FIG. 10A illustrates a surgical clip base 405 having opposing legs 412 and 414 adapted to receive clamp arms 425 and 430. Although any of the generally flat constructions discussed above would be suitable, clip base 405 is preferably formed of a surgical grade wire having any suitable cross-sectional shape. Clip base 405 includes an elastic connecting portion 415 and will be formed to have a central opening 420. In a preferred embodiment, clip base 405 is made of a wire having a relatively square cross-section.

Figure 10C:
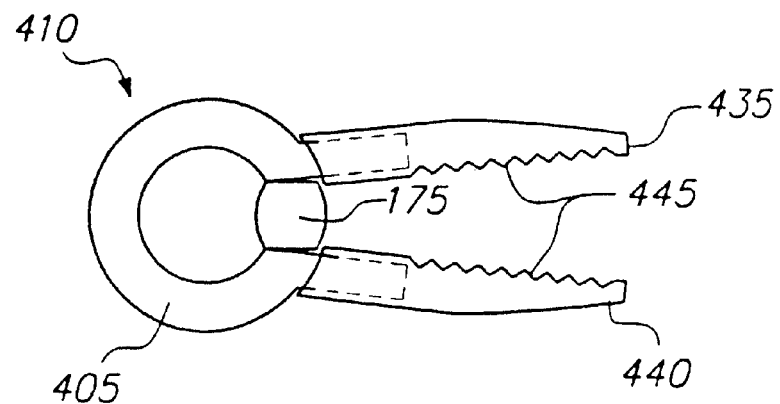
Figure 17:
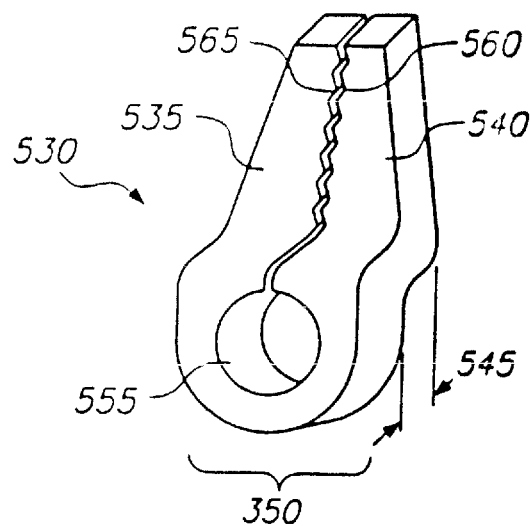
FIG. 17 is a perspective view of a surgical clip having an offset construction according to the principles of the present invention.

One advantage of this construction is that the clip arms may be made of a different material than the connecting portion. Thus, the clip base material may be selected for optimal spring properties and the clamp arms may be of a material that allows easy manufacture of the desired clamp arm features. In addition, a single clip base could be made to support clip arms adapted for a number of varied uses. FIG. 10C illustrates an assembled surgical clip 410 with clamp arms 435 and 440 having an optional reduced arm profile and optional transverse clamping teeth 445.

Connecting portion 415 is sized to provide the desired elastic force at legs 412 and 414 and thus to clamp arms 425 and 430 connected thereto. The clamp arms may be held open by way of a locking feature on clip base 405 or on one or both of clamp arms 425 and 430. The clamp arms may alternatively be held open by way of a secondary member, such as pin 175. Surgical clip 400 is then released to a closed position simply by displacing pin 175. Central opening 420 is preferably sized to accommodate removal of the secondary member after it has been displaced to close the surgical clip.

The present invention may also be of a single wire construction. FIGS. 11A and 11B show surgical clip 450 constructed of a single wire. Surgical clip 450 includes clamp arms 455 and 460 proximally joined by connecting member 465. The connecting member may be of any shape that provides the desired forces at the clamp arms. Connecting member 465 illustrates a triangular shape symmetrically centered about the longitudinal axis of the clamping plane created by clamp arms 455 and 460.

FIGS. 12A and 12B illustrate surgical clip 470 having connecting portion 475 in the form of a right triangle extending directly from clamp arm 460. FIGS. 13A and 13B illustrate surgical clip 480 with connecting portion 485 in the form of a modified right triangle having a curved section 490. With each configuration, clamp arms 455 and 460 are normally closed, may be forced to an open position, and may be locked in that open position using a locking mechanism or secondary member, such as a pin or ring as discussed above.

To improve the deflection and stress characteristics of the connecting portion of the surgical clip, it may be desirable to construct the portion connecting the clamp arms in a non-planar or multi-turn configuration, such as a spiral or helical wound spring element. Examples of surgical clips having a connecting portions in the form of a helical wound torsion springs are shown in FIGS. 14A–16B.

FIGS. 14A–14C illustrate a wire material surgical clip 500 having clamp arms 455 and 460 connected by connecting portion 495 in the form of a spiral or helical wound spring. Clamp arm 455 generally proceeds proximally directly into the formation of the first turn of the connection portion 495. Clamp arm 460 which generally proceeds distally out from the last turn of connecting portion 495 at an offset substantially equal to the number of turns times the diameter of the wire. An angled or bent portion 457 must be added to clamp arm 460 so that the distal portions of clamp arms 455 and 460 line up to provide proper clamping. Surgical clip 500 is constructed to have proximal opening 459 to facilitate removal of any secondary element used to lock surgical clip 500 into an open position in the manner described at length above.

FIGS. 15A and 15B show a variation of surgical clip 500. Surgical clip 510 has clamp arms 455 and 460 substantially centered in the width of connecting spring member 505. To have the clamp arms 455 and 460 centered in the manner shown, each clamp arm 455 and 460 will have a proximal bent section 509 and 507, respectively, leading into the coils of the connecting spring member 505. Again, the wire material forming surgical clip 510 may be formed to have a proximal space 511 to facilitate the removal of any secondary member used to lock surgical clip 510 into an open position.

FIGS. 16A and 16B illustrate surgical clip 525 having an alternate clamp arm arrangement. Surgical clip 525 has a lower clamp arm 520 and an upper clamp arm 515 connected by connecting spring member 505. Upper clamp arm 515 is generally centered within the width of connecting member 505 by way of a bent or angled section 524. Lower clamp arm 520 is a U-shaped member having a first leg 527 extending directly from last coil of spring member 505, and a spaced second leg 529 generally parallel to first leg 527. With this configuration the alignment of the opposing clamp arms are much less critical since upper clamp arm 515 will be somewhat self centering between the first and second legs 527 and 529 of lower clamp arm 520. Surgical clip 525 includes proximal space 522 to facilitate removal of any secondary member used to lock surgical clip 510 into an open position.

As previously noted, the surgical clips described above may be opened, using a supplemental fixture if desired, and locked into an open position prior to loading into and subsequent delivery by a properly constructed clip applicator. Among other things, this allows the often substantial forces required to separate and open the clamp arms to be borne mechanically by a device or fixture separate from the clip applicator, leaving the clip applicator only to actuate the locking mechanism or displace the secondary member. In another aspect of the present invention the surgical clips may be loaded into a clip applicator in their normally closed position, opened by action of the clip applicator, and then released over a desired structure. In a preferred embodiment, multiple clips may be loaded into a clip applicator and delivered by a simple tubular member having a pusher, plunger, or other simplified mechanism.

Figure 19A:
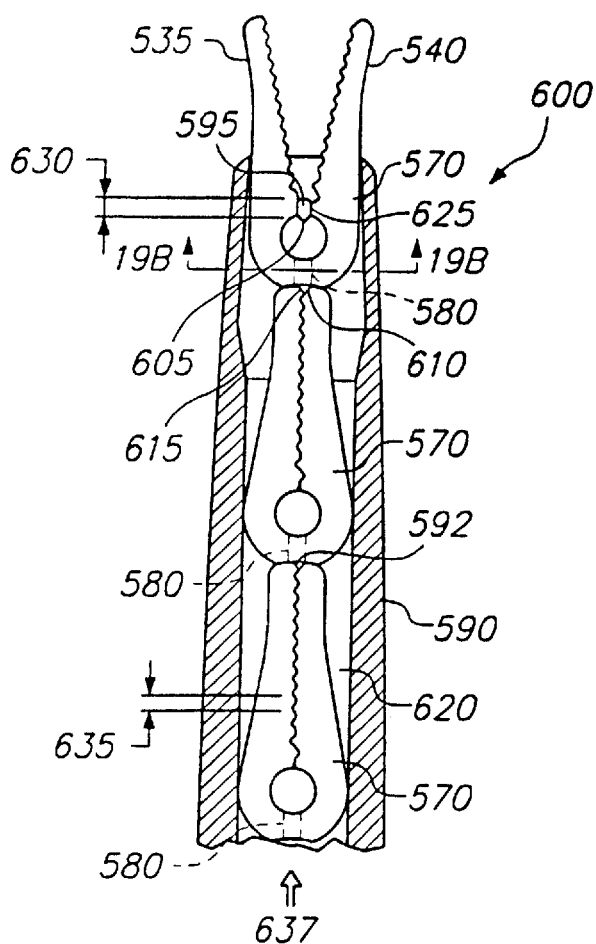
FIG. 19A is front view in partial cross-section illustrating a clip applying system according to the principles of the present invention.
Figure 19B:
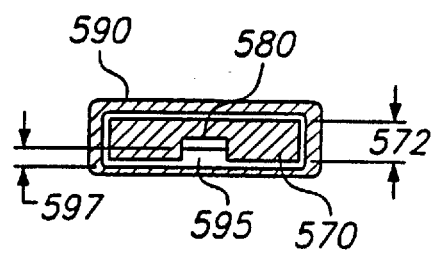
FIG. 19B is a cross-sectional view of the clip applying system of FIG. 19A taken along line 19B—19B.

A preferred normally closed surgical clip and surgical clip delivery system for delivering one or more surgical clips is illustrated in FIGS. 19A and 19B. Clip applying system 600 includes delivery tube 590 having an inner cavity or central lumen 620 adapted to receive one or more surgical clips 570. Preferably, the surgical clips are situated in a line such that the distal end of each clip is aligned against the proximal end of the clip directly in front of it. Surgical clip 570 has a sufficiently small clearance within central lumen 620 such that the entire line of clips may be pushed in the direction of arrow 637 without the clips becoming misaligned or jamming within central lumen 620. To help keep the clips aligned as they are advanced through central lumen 620, a small recess or cutout 592 in the proximal portion of each clip may optionally be adapted to at least partially receive a distal portion of an adjacent surgical clip.

Disposed at or near the distal most end of delivery tube 590 is an actuator pin 595. Actuator pin 595 has a leading portion 605 which is pointed or angled to engage the small spacing between clamp arms 535 and 540 such as to begin to force the clamp arms apart as the surgical clip 570 is advanced in the direction of arrow 637. Preferably, the distal ends of clamp arms 535 and 540 have lead-in angles or chamfers 615 and 610, respectively, to further facilitate initiation of actuator 595 between clamp arms 535 and 540. If the inner clamping surfaces of clamp arms 535 and 540 have transverse clamping features, such as teeth 560 and mating recesses 565, actuating pin 595 is preferably constructed to have a longitudinal dimension 630 greater than the maximum distance 635 between transverse teeth 560.

FIG. 19A shows clip 570 in its final position, having been advanced over pin 595 such that clamp arms 535 and 540 are held open at surface 625 against pin 595. From that position, further distal displacement of clip 570 disengages surfaces 625 from pin 595, allowing clamp arms 535 and 540 to close. Surfaces 625 may optionally include a detent mechanism which cooperates with pin 595 to stop or impede further advancement of clip 570 over pin 595 when clip 570 has reached the final position. In one embodiment, at least a portion of surface 625 is concave to accept at least a portion of pin 595 in the manner of a detent mechanism.

After closure (not shown) clip 570 is positioned with central opening 555 generally around pin 595. To allow clip 570 to completely disengage from the clip applicator, pin 575 must be allowed to clear connecting portion 575. This may be accomplished by mounting pin 595 on a flexure or the like to allow it to deflect out of the way of connecting portion 575, or the surgical clip itself may be configured to allow clearance for pin 595 in some manner past or through connecting portion 575.

Figure 18:
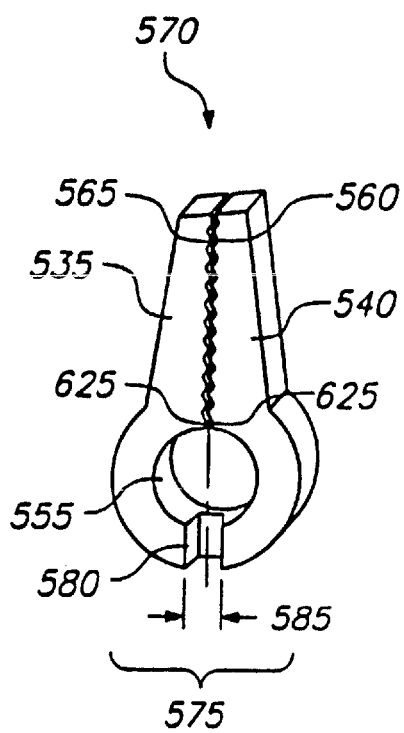
FIG. 18 is a perspective view of a surgical clip having a proximal channel according to the principles of the present invention.

In a preferred embodiment best shown in FIG. 18, surgical clip 570 include a clearance cutout or channel 580 through connecting portion 575 having a width 585 sufficient to allow clearance for the proximal portion of surgical clip 570 to pass over pin 595. Preferably, pin 595 has a height 597 which is less than the thickness 572 of pin 595, most preferably, height 597 is about 50% or less of thickness 572.

In another embodiment, the surgical clip may be formed such that the proximal portion joining the clamp arms does not interfere with passage of the clip over the stationary pin. For example, the connecting portion may be configured at an angle to the plane of the clamp arms (i.e., a right angle) or may be otherwise offset from the plane of the clamp arms.

Surgical clip 530 illustrates a clip configuration in which the connecting portion 550 is offset from clamp arms 535 and 540. The offset distance 545 is selected to be greater than the height of pin 595. In a preferred embodiment, offset distance 545 is substantially equal to the thickness of surgical clip 530. This allows the distal end of each surgical clip to be positioned under the connecting portion of a forward positioned surgical clip as the clips are loaded in an end to end fashion within the central lumen 620 of delivery tube 590.

The surgical clips and clip applicator system described above allow sequential application of surgical clips without bulky or complex mechanism in the area of the clamping arms. In the preferred embodiment shown in FIG. 19A, clamp arms 535 and 540 extend from delivery tube 590 completely unobstructed by any mechanism. Thus the surgeon's view of the clamping arms and structure to be clamped is optimized. Further, the delivery system requires motion and force to be applied only in the axial direction indicated by arrow 637 to actuate each clip in sequence, eliminating the need for complex opening and closing distal jaw mechanisms.

Figure 20:
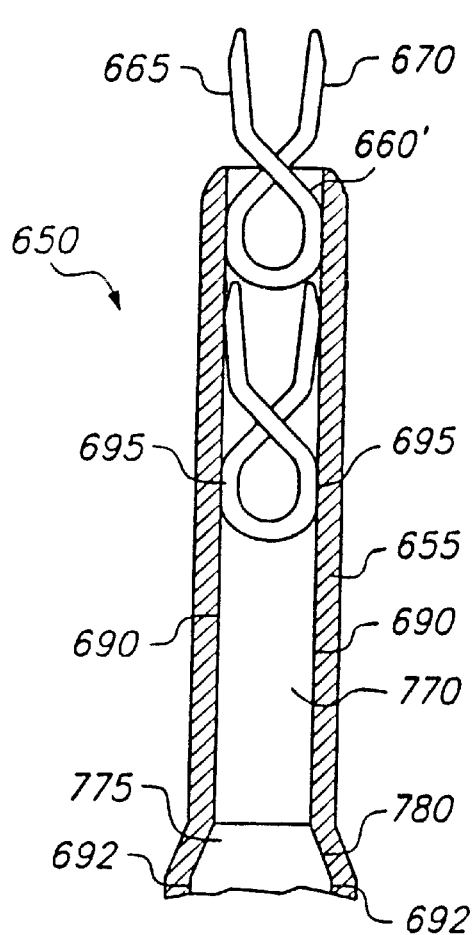
FIG. 20 is a top view in partial cross-section illustrating a clip applicator holding a surgical clip in an operatively open position according to the principles of the present invention.
Figure 21:
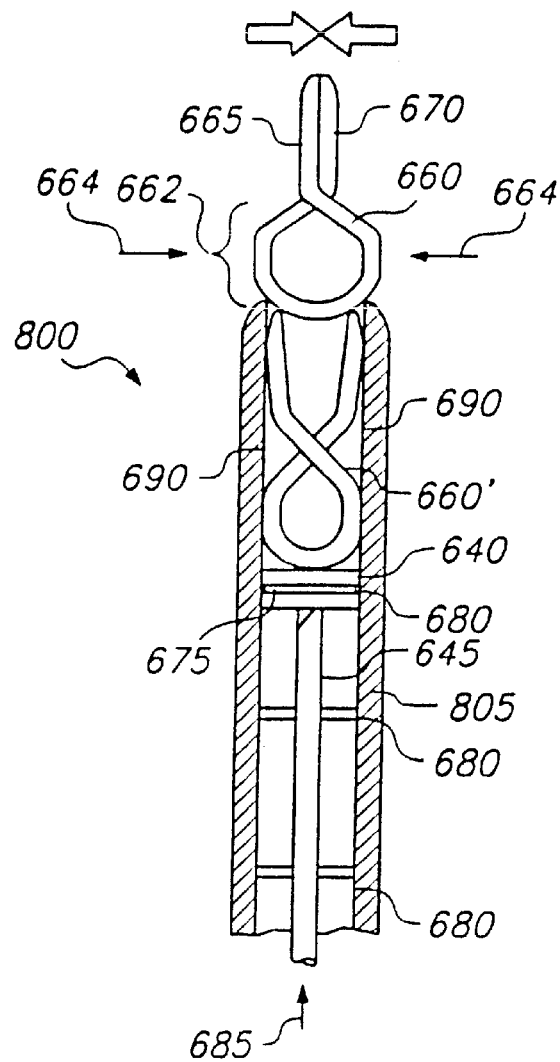
FIG. 21 is a top view in partial cross-section illustrating the clip applicator of FIG. 20 and the clip after release in its closed position.

Another surgical clip and clip applicator system which requires no mechanism in the area of the clamp arms and requires only simple motion for actuation is shown in FIGS. 20 and 21. The surgical clip may be a normally closed, wire clip having a connecting portion that, when compressed by an external force, tends to urge the clamps arms to an open position. The clip applicator has features that holds one or more wire clips in the compressed and opened position until released distally from the applicator.

In a preferred embodiment, surgical clip 660 has opposing clamp arms 665 and 670 biased into a normally closed position by connecting member or portion 662. Surgical clip 660 is opened simply by compressing the sides of connecting portion 662 as generally indicated by arrows 664. The clip applicator system has a delivery tube 655 having at least one internal lumen adapted to receive one or more surgical clips 660. The lumen is generally configured to have parallel sides 690 adapted to constrain the clip in the opened position. Connecting portion 664 may also have flat side 695 to mate with parallel sides 690 of delivery tube 655.

In a preferred embodiment, delivery tube 655 has a first tube section 770 having substantially parallel sides 690 spaced apart such that clip 660 is held in the desired open position (660'). Delivery tube 655 may also have a second tube section 775 having opposing sides 692 spaced apart a larger distance. This allows clips to be loaded into tube section 775 in their normally closed state and then opened as they are advanced into tube section 770, preferably using an angled transition section 780. To reduce the amount of friction required to push a series of end to end surgical clips, the length of first tube section 770 may be relatively short, preferably holding only one or two clips in the opened position.

The surgical clips held in the open position (660') may be ejected and released by any mechanism suitable to push or advance the surgical clips in the direction indicated by arrow 685 until connecting portion 664 emerges distally from the confines of constraining sides 690. At that point, connecting portion 664 springs back to its non-compressed configuration, thus closing clamp arms 665 and 670. Clip applicator system 800, for example, illustrates an ejector mechanism in the form of a plunger 680 attached to a shaft 645.

Surgical clips 660 are advanced distally by advancing shaft 645 in the direction indicated by arrow 685. The ejector mechanism may also include a series of detent mechanisms which tend to stop or inhibit further advancement of plunger 680 after each surgical clip has been released. In one embodiment, plunger 680 has a recess, groove, or indent 675 which operates in conjunction with one or more raised features 680 in the manner of a detent mechanism.

Figure 22:
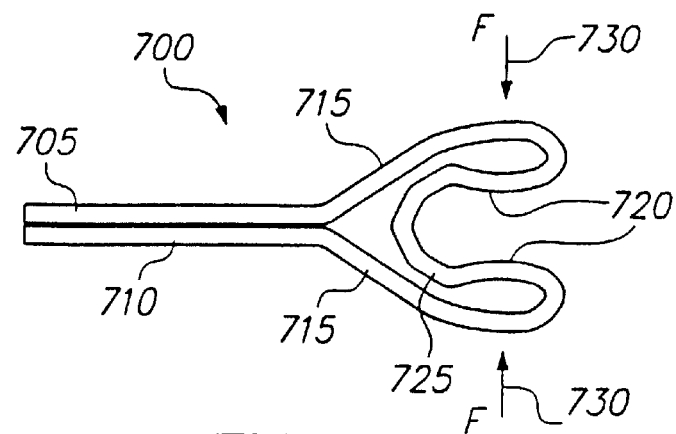
FIG. 22 is a front view of an alternate surgical clip construction.

Although clip ejector systems 650 and 800 have been described with reference to a preferred clip 660, a variety of normally closed clips would be suitable for delivery using these preferred applicator systems. An alternate normally closed, wire surgical clip suitable for delivery using the above described clip applicator systems is shown in FIG. 22. Surgical clip 700 has clamp arms 705 and 710 having a connecting portion which includes first flexures 715 and second internal flexures 720 connected by wire section 725. The additional flexure elements allows an increased amount of deflection with lower stresses as the clip is compressed by a compression force, F, as indicated by arrows 730.

Figure 24:
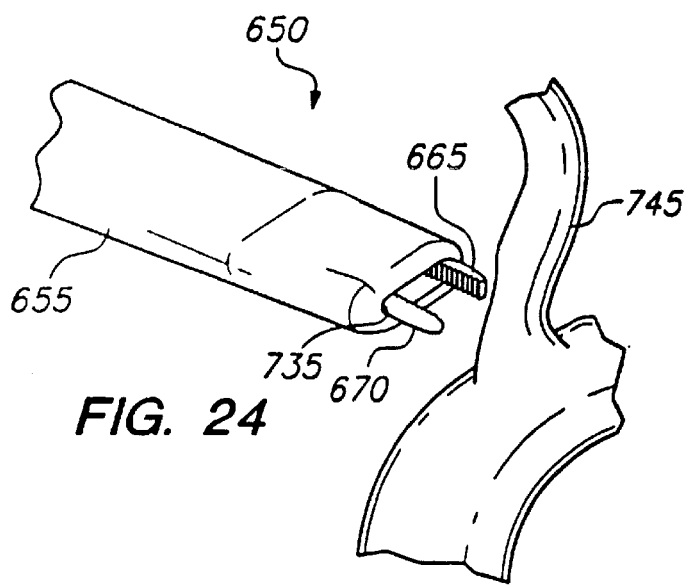
FIG. 24 is a perspective view of a clip applicator system illustrating a surgical clip in a pre-release, open position.
Figure 25:
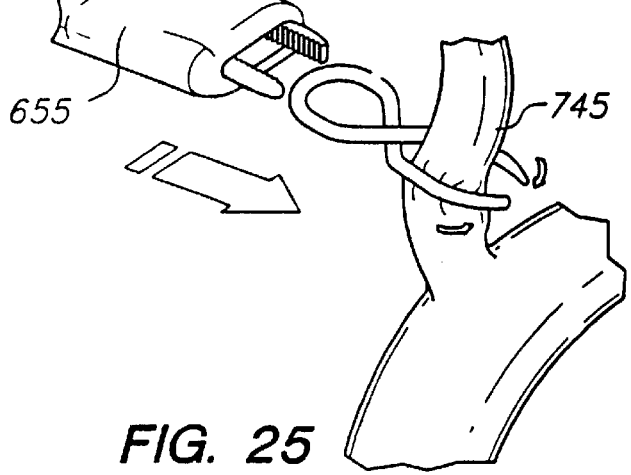
FIG. 25 is a perspective view of the clip applicator system of FIG. 24 illustrating a surgical clip released and closed upon a target branch vessel.

The preferred clip applicator system 650 (or 800) allows the surgical clips to be delivered to the target structure without resort to complicated or bulky jaw mechanisms which would tend to obstruct the view of the clamp arms. In operation, when surgical clip 660 is in the final position within delivery tube 655, at least a portion of clamp arms 665 and 670 extend unobstructed from distal opening 735. As shown in FIGS. 24 and 25, the clamp arms may be easily positioned over the desired structure, such as branch vessel 745, and released by advancing the clip distally until connecting portion 664 exits distal opening 735 of delivery tube 665. Upon exit from delivery tube 665, connecting portion 664 is then allowed to elastically expand, thus closing clamp arms over the branch vessel as illustrated in FIG. 25. At the same time one surgical clip is released, the next clip is advanced to the final position ready for placement.

Figure 23:
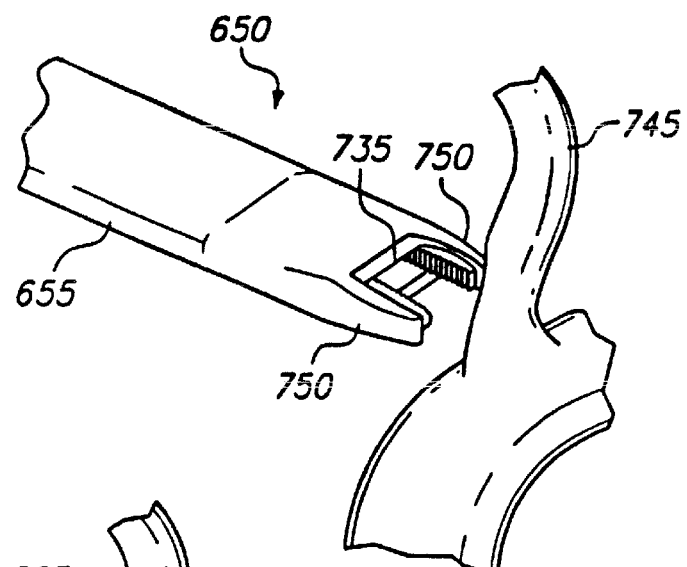
FIG. 23 is a perspective view of a clip applicator system having distal support features illustrating a surgical clip in a pre-release, open position.

Because surgical clip 660 is held in the final position primarily only by the friction between sides 695 of connecting portion 664 and internal surfaces 690 of delivery tube 655, it may sometimes be desirable to include distal guides 750 (FIG. 23) to protect clip 660 from accidental displacement as the delivery system is manipulated into the desired position within the body. Distal guides 750 are preferably thin members extending distally of opening 735 which provide support to clamp arms 665 and 670.

Figure 26:
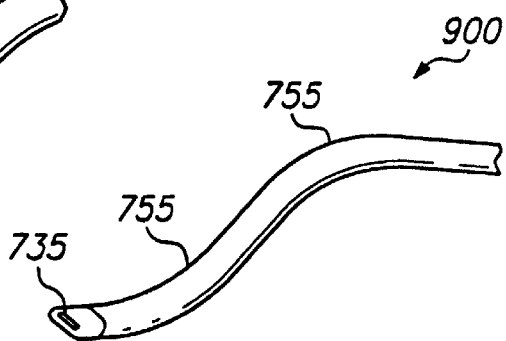
FIG. 26 is a perspective view of the distal end of a clip applicator having a deformable shaft section.

While the clip application systems of the present invention have been described, for purposes of illustration only, with reference to delivery tubes that have relatively straight configurations, the delivery tubes may well have any configuration which is convenient for the intended surgical procedure. For example, the delivery tube may have distal sections that are permanently angled or curved or may have sections that are deformable or shapeable. Referring to FIG. 26, delivery tube 900 is shown as having a shapeable or malleable section 755, that allows the surgeon to position distal opening 735 to any desired orientation.

While certain embodiments are illustrated in the drawings and have just been described herein, it will be apparent to those skilled in the art that many modifications can be made to the embodiments without departing from the inventive concepts described. For purposes of illustration only, certain principles of the present invention have been described with reference to clamping or ligating branch vessels of the IMA or saphenous vein, but such principles may readily be applied to other types of surgical procedures not specifically described. Many other uses are well-known in the art, and the concepts described herein are equally applicable to those other uses. Further, the different components of the various exemplar embodiments described above can be combined in any desirable construction. Accordingly, the invention is not to be restricted except by the claims which follow.

What is claimed is:

1. A surgical clip for clamping a target structure comprising:
   a pair of clamp arms having mating clamping surfaces and including a resiliently-biased element disposed to resiliently bias the mating clamping surfaces toward engagement in substantially parallel, closed relationship for clamping said target structure; and
   a member engaging the mating clamping surfaces for selectively retaining the mating clamping surfaces disengaged in an open position to facilitate positioning of the mating clamping surfaces about the target structure, and for returning the mating clamping surfaces to the closed relationship in response to selective disengagement of the member with said mating clamping surfaces.

2. A surgical clip according to claim 1 in which the member is disposed to selectively disengage the mating clamping surfaces along a direction that is substantially normal to or oriented within a plane of movement of the clamping surfaces between the open and closed relationships thereof.

3. A method of applying to a target tissue structure a surgical clip having mating clamping surfaces resiliently biased toward closed clamping engagement including a member that selectively controls the manipulation of the surgical clip relative to the target tissue structure between closed clamping and open unclamping conditions, the method comprising:
   engaging the member with the clamping surfaces of the surgical clip to overcome the resilient bias to selectively retain the clamping surfaces of the surgical clip in open unclamping conditions;
   positioning said target tissue structure between the clamping surfaces of the surgical clip with the clamping surfaces selectively retained in open unclamping condition; and
   manipulating the member relative to the surgical clip for selectively enabling the resilient bias to urge the mating clamping surfaces toward closed clamping engagement about the target tissue structure.

4. The method according to claim 3 wherein:
   selectively enabling resilient bias includes altering the position of the member relative to the surgical clip to release the resilient bias for urging the clamping surfaces toward mating engagement.

5. The method according to claim 3 in which the member is interposed between the clamping surfaces; and
   manipulating the member includes removing the member from between the clamping surfaces.

6. The method according to claim 5 in which the member is removed from between the clamping surfaces along a direction that is substantially normal to or oriented within a plane of movement of the clamping surfaces between clamping and unclamping conditions.

* * * * *